US010078093B2

(12) United States Patent
Flagle et al.

(10) Patent No.: US 10,078,093 B2
(45) Date of Patent: Sep. 18, 2018

(54) SYSTEM FOR IMPROVED TISSUE HANDLING AND IN LINE ANALYSIS OF THE TISSUE

(71) Applicant: Hologic, Inc., Marlborough, MA (US)

(72) Inventors: Jacob Flagle, New Palestine, IN (US); Chia Yee Ang, Avon, IN (US); Kenneth F. Defrietas, Patterson, NY (US); Ian Shaw, Yorktown Heights, NY (US); John Laviola, Orange, CT (US); Samantha Perkins, Avon, IN (US); Zachary R. Nicoson, Zionsville, IN (US)

(73) Assignee: HOLOGIC, INC., Marlborough, MA (US)

( * ) Notice: Subject to any disclaimer, the term of this patent is extended or adjusted under 35 U.S.C. 154(b) by 67 days.

(21) Appl. No.: 15/410,669

(22) Filed: Jan. 19, 2017

(65) Prior Publication Data

US 2017/0131311 A1 May 11, 2017

Related U.S. Application Data

(63) Continuation of application No. 14/284,634, filed on May 22, 2014, which is a continuation of application
(Continued)

(51) Int. Cl.
*G01N 35/04* (2006.01)
*A61B 6/00* (2006.01)
(Continued)

(52) U.S. Cl.
CPC ............ *G01N 35/04* (2013.01); *A61B 6/4405* (2013.01); *A61B 10/0096* (2013.01);
(Continued)

(58) Field of Classification Search
CPC ............ A61B 10/0275; A61B 10/0283; A61B 2010/0225
See application file for complete search history.

(56) References Cited

U.S. PATENT DOCUMENTS

| | | | |
|---|---|---|---|
| 4,038,988 | A | 8/1977 | Perisse |
| 4,134,012 | A | 1/1979 | Smallbone et al. |

(Continued)

FOREIGN PATENT DOCUMENTS

EP 2007287 B1 6/2016

OTHER PUBLICATIONS

International Search Report and Written Opinion for PCT Appln. Serial No. PCT/US11/62107, Applicant Hologic, Inc., dated May 25, 2012, 13 pages.
(Continued)

*Primary Examiner* — Adam J Eiseman
(74) *Attorney, Agent, or Firm* — Vista IP Law Group LLP

(57) ABSTRACT

A system for analysis of biopsy samples includes a tissue sample transport mechanism linking a biopsy sample excision tool to a tissue sample holder disposed in a staging area of an analysis unit. The tissue sample is automatically transported from the excision tool to the specimen holder, where the tissue sample is analyzed in the staging area of the analysis unit. The transport mechanism may include tubing and a vacuum source. The tissue sample holder may be configured to slow or temporarily stop a tissue sample for individual analysis, or collect multiple tissue samples for analysis as a group. A tissue sample sorting mechanism may be employed that allows separation of specimens that can be correlated to the analysis.

20 Claims, 34 Drawing Sheets

Related U.S. Application Data

No. 13/383,318, filed as application No. PCT/US2011/062148 on Nov. 24, 2011, now Pat. No. 9,492,130.

(60) Provisional application No. 61/417,096, filed on Nov. 24, 2010.

(51) Int. Cl.
*A61B 10/02* (2006.01)
*A61B 10/00* (2006.01)
*B01L 3/00* (2006.01)

(52) U.S. Cl.
CPC .......... *A61B 10/0283* (2013.01); *B01L 3/502* (2013.01); *B01L 2200/025* (2013.01); *B01L 2200/026* (2013.01); *B01L 2200/0684* (2013.01); *B01L 2300/021* (2013.01); *B01L 2300/025* (2013.01); *B01L 2300/0681* (2013.01); *B01L 2400/049* (2013.01); *B01L 2400/0605* (2013.01); *B01L 2400/0644* (2013.01); *G01N 2035/0481* (2013.01)

(56) References Cited

U.S. PATENT DOCUMENTS

| | | |
|---|---|---|
| 4,306,570 A | 12/1981 | Matthews |
| 4,658,834 A | 4/1987 | Blankenship et al. |
| 4,837,795 A | 6/1989 | Garrigus |
| 5,256,160 A | 10/1993 | Clement |
| 5,491,344 A | 2/1996 | Kenny et al. |
| 5,505,210 A | 4/1996 | Clement |
| 5,526,822 A | 6/1996 | Burbank et al. |
| 5,575,293 A | 11/1996 | Miller et al. |
| 5,983,125 A | 11/1999 | Alfano et al. |
| 6,322,522 B1 | 11/2001 | Zimmon |
| 6,403,035 B1 | 6/2002 | Caratsch et al. |
| 6,485,436 B1 | 11/2002 | Truckai et al. |
| 6,535,284 B1 | 3/2003 | Hajduk et al. |
| 7,715,523 B2 | 5/2010 | Lafferty |
| 7,753,857 B2 | 7/2010 | Hibner |
| 7,758,601 B2 | 7/2010 | Heywang-Koebrunner et al. |
| 7,858,038 B2 | 12/2010 | Andreyko et al. |
| 8,052,616 B2 | 11/2011 | Andrisek et al. |
| 2002/0193656 A1 | 12/2002 | Ravins et al. |
| 2003/0216730 A1 | 11/2003 | Barry et al. |
| 2004/0218716 A1 | 11/2004 | Freifeld |
| 2005/0051723 A1 | 3/2005 | Neagle et al. |
| 2005/0124913 A1 | 6/2005 | Damarati |
| 2006/0074343 A1 | 4/2006 | Hibner |
| 2006/0116603 A1 | 6/2006 | Shibazaki et al. |
| 2006/0173266 A1 | 8/2006 | Pawluczyk et al. |
| 2007/0166834 A1 | 7/2007 | Williamson, IV et al. |
| 2007/0270714 A1 | 11/2007 | Cushner et al. |
| 2008/0004545 A1 | 1/2008 | Garrison |
| 2008/0132805 A1 | 6/2008 | Heywang-Koebrunner et al. |
| 2008/0214955 A1 | 9/2008 | Speeg et al. |
| 2008/0221480 A1 | 9/2008 | Hibner et al. |
| 2009/0088663 A1 | 4/2009 | Miller et al. |
| 2009/0088666 A1 | 4/2009 | Miller et al. |
| 2009/0131818 A1 | 5/2009 | Speeg et al. |
| 2009/0131823 A1 | 5/2009 | Andreyko et al. |
| 2009/0171244 A1 | 7/2009 | Ning et al. |
| 2009/0213987 A1 | 8/2009 | Stein et al. |
| 2010/0081964 A1 | 4/2010 | Mark et al. |
| 2010/0152611 A1 | 6/2010 | Parihar et al. |
| 2010/0191145 A1 | 7/2010 | Lafferty et al. |
| 2012/0116246 A1 | 5/2012 | Hibner et al. |
| 2012/0123295 A1 | 5/2012 | Sanbuichi |
| 2014/0039343 A1 | 2/2014 | Mescher et al. |

OTHER PUBLICATIONS

International Search Report and Written Opinion, corresponding PCT Appln. No. PCT/US11/62148 dated Mar. 12, 2012, 9 pp.
Extended European Search Report for EP Appln. No. 11845127.7, dated Nov. 25, 2017 (8 pages).

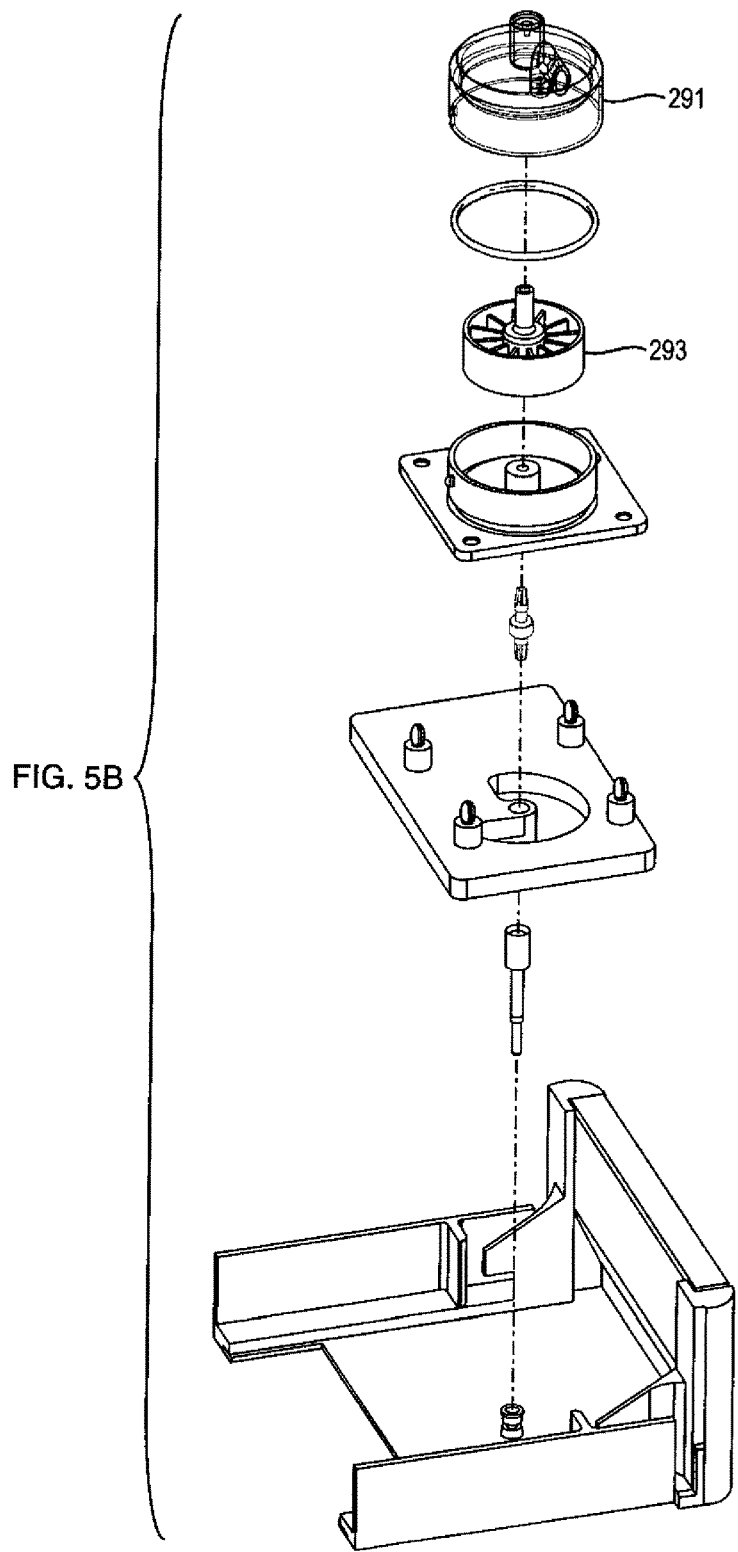

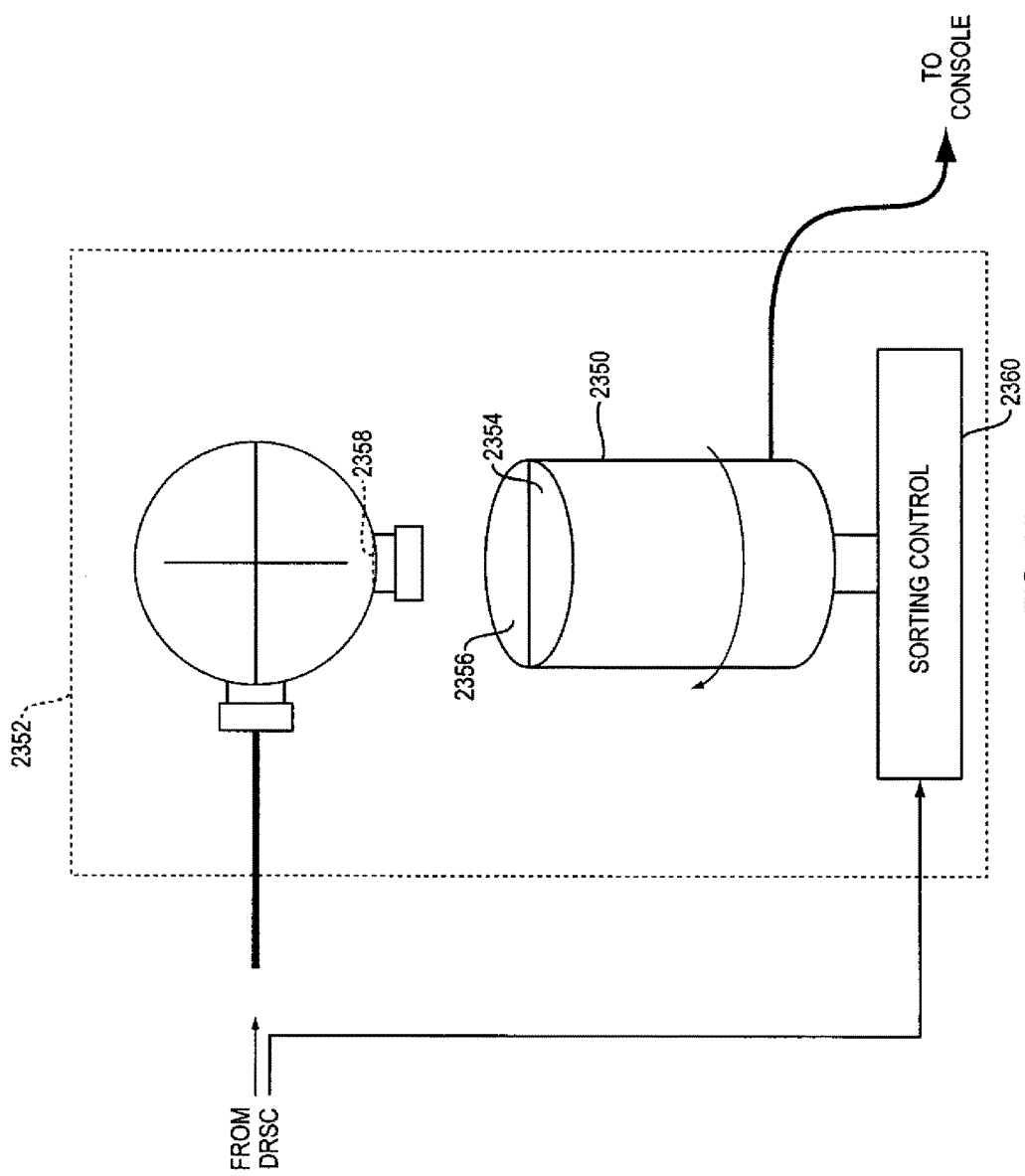

SYSTEM FOR IMPROVED TISSUE HANDLING AND IN LINE ANALYSIS OF THE TISSUE

CROSS-REFERENCE TO RELATED APPLICATIONS

The present application is a continuation of pending U.S. patent application Ser. No. 14/284,634, filed May 22, 2014, which is a continuation of U.S. patent application Ser. No. 13/383,318, filed Jan. 10, 2012, now issued as U.S. Pat. No. 9,492,130, which is a National Phase entry under 35 U.S.C. § 371 of International Application No. PCT/US2011/062148, filed Nov. 24, 2011, which claims the benefit under 35 U.S.C. § 119 to U.S. Provisional Application Ser. No. 61/417,096, filed Nov. 24, 2010, entitled SYSTEM AND METHOD FOR REAL-TIME X-RAY IMAGING AND CALCIFICATION HIGHLIGHTING OF BIOPSY SAMPLES DURING BIOPSY PROCEDURES. The foregoing applications are hereby incorporated by reference into the present application in their entirety.

FIELD OF THE INVENTION

Aspects of this invention relate generally to analysis of tissue samples, and more particularly to preparing samples for analysis and providing near real time or real time analysis of the tissue sample.

BACKGROUND

Screening exams and biopsies are used to detect cancer and other diseases. For example, a mammogram may be obtained to perform a breast cancer screening exam. If an abnormality is detected during the screening exam then a biopsy may be performed. One form of breast abnormality which may be indicative of cancer is the presence of micro-calcifications within the breast. In the case of a breast biopsy, the patient is positioned so that the area of interest associated with the abnormality can be localized, and one or more biopsy or "core" tissue samples obtained using a biopsy needle.

The tissue samples are then extracted from the needle and placed on a specimen tray. An operator, such as a radiologist, then arranges the samples on the specimen tray. These steps are made more difficult because the samples may be tightly intertwined against each other, and small parts must be manipulated by the operator while wearing protective gloves. Once the samples are arranged on the specimen tray, the tray is transported to an x-ray machine which may be in a different room. Finally, the x-ray images must be examined by skilled personnel for the presence of microcalcifications or other abnormalities.

Micro-calcifications are easily seen in x-ray images. The presence of calcifications in the captured images is indicative of accurate targeting of the area of interest and the potential presence of cancer. The absence of calcifications in tissue samples is inconclusive because it can indicate either that the area of interest is free of calcifications or that incorrect or insufficient tissue has been biopsied to present the calcifications. When samples with calcifications are not obtained the biopsy procedure may need to be repeated, i.e., a second pass biopsy. A second pass biopsy is generally undesirable because it increases the amount of time the patient is in compression and the overall procedure time.

When the biopsy procedure is completed the tissue samples are sent to a pathology lab for further analysis. In many cases, the user will separate the cores with calcifications, place them in a separate specimen jar, and label as such for the pathologist. This is accomplished by comparing the specimen tray with cores, to the X-ray or radiograph of the specimen tray with cores. The radiograph can then be correlated to the actual specimen tray and cores. The user is then able to separate the cores with calcifications and place them into a formalin jar. The cores without calcifications are then placed in a separate formalin jar. This process requires a large amount of manipulation of the cores and requires a fair amount of human intervention.

It is known to decrease the amount of time required to perform a biopsy by using a Radiography Specimen Cabinet (RSC). RSCs are relatively small portable self-contained imaging systems used to obtain images of small to medium sized tissue samples following tissue removal. A RSC can be located close to the location of the patient during the biopsy procedure, e.g., in the same room, thereby reducing the time required to transport the samples to x-ray imaging equipment. However, the time required to remove and arrange the samples for imaging is still relatively long.

SUMMARY

In accordance with one aspect of the invention an apparatus comprises: a specimen holder that is able to receive excised tissue from a biopsy device, the specimen holder adapted to fit within a staging area of an analysis unit to enable analysis of excised tissue.

In accordance with another aspect of the invention an analysis system comprises: an energy source; an energy detector; a staging area, positioned between the source and the detector and adapted to contain a specimen holder, wherein a specimen is transported to the specimen holder from a biopsy device and imaged in the specimen holder using the source and detector.

In accordance with another aspect of the invention a biopsy device comprises: a cannula for cutting tissue; a first port on the cannula for coupling to a fluid supply system; a second port for coupling to a vacuum system; and a venting system, the venting system controlled to assist movement of tissue from the biopsy device to a specimen radiograph for analysis of the tissue.

In accordance with another aspect of the invention a method comprises: extracting a tissue specimen with a biopsy device having an inner cannula and an outer cannula, the extracted specimen being disposed in the inner cannula; transporting the tissue from the inner cannula to a specimen holder disposed within a staging area of an analysis unit; and analyzing the specimen.

In accordance with another aspect of the invention a apparatus comprises: a specimen holder that is able to receive excised tissue from a biopsy device, wherein the specimen holder, or portion of, can be removed from the biopsy device and allow analysis of the specimen holder, or portion of, and captured tissue while providing an analysis substantially free of artifacts.

Some features and benefits of aspects of the invention include providing a analysis of each tissue sample core as it is obtained with the biopsy device in order to provide near real time feedback to the physician during the procedure, and providing a core handling feature to help reduce or eliminate the need to manipulate specimens from biopsy through placement into a specimen jar while enabling communication to the pathologist which cores have calcifications. Other aspects of the invention help to match particular tissue samples with corresponding images. Still other aspects of the invention at least partially automate sorting of tissue samples based on a particular characteristic. These and other aspects of the invention are advantageous because they help to reduce the duration of a biopsy procedure, reduce the number of second pass biopsies, reduce the amount of tissue excised during a biopsy procedure, and reduce the overall cost of providing patient care.

BRIEF DESCRIPTION OF THE DRAWINGS

FIGS. 5A and 5B are diagrams of a RSC and specimen holder of the present invention, provided to illustrate the ease of access to the specimen holder in the staging area.

FIG. 25 illustrates a variation of the embodiment of FIG. 24.

DETAILED DESCRIPTION

Figure 1:
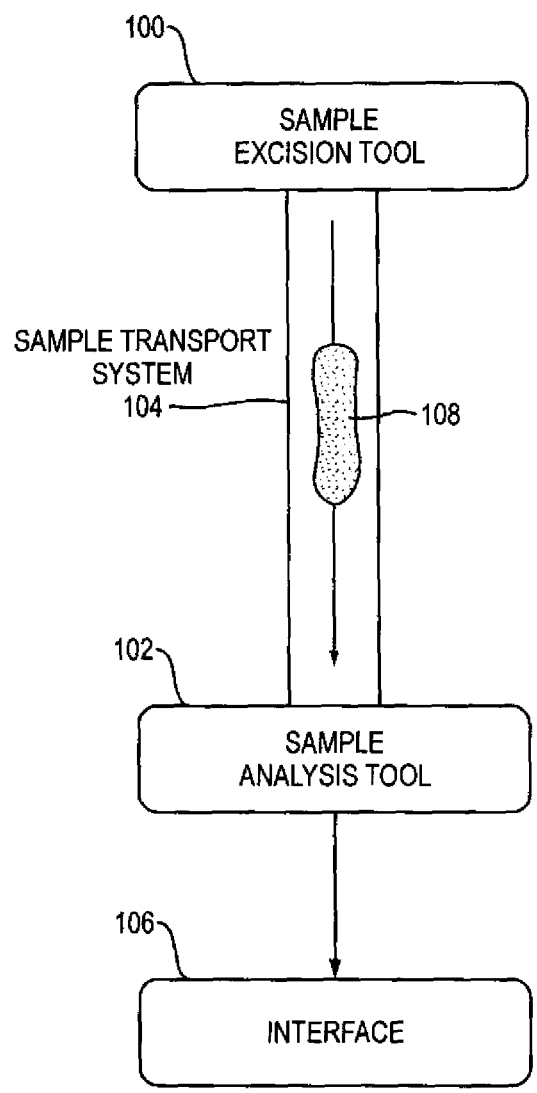
FIG. 1 is a block diagram of a system for inline tissue sample transport and imaging for real-time tissue analysis during a biopsy procedure.

FIG. 1 is a block diagram of a system for inline sample transport and imaging for real-time analysis of biopsy samples. A biopsy sample excision tool 100 such as a biopsy device is coupled to a sample analysis tool 102 such as an x-ray imaging station via an automated sample transport system 104. A tissue sample is obtained from the patient using the excision tool 100. The sample transport system 104 moves the excised tissue sample 108 from the excision tool to the analysis tool. The transport system is "inline" because the tissue sample is moved into position to be imaged without the need for manual transport and arrangement, or with minimal need for manual intervention. Results from the imaging, e.g., radiograph and possibly highlighting of calcifications, if present, are then provided via an interface 106 such as a display. Calcifications normally appear in x-ray images as an area characterized by a contrast in brightness, but highlighting on the interface may include automated detection and flagging of calcifications or other indicators in images using image processing algorithms. The analysis or radiograph is "near real time" because the results can be presented during the biopsy procedure, e.g., within seconds of tissue excision, or prior to excision of a subsequent core sample, or simply in less time than the current time for prepping cores and obtaining a radiograph. Consequently, the physician has more information during the procedure to help obtain the target calcifications. Alternatively, any type of analysis could be conducted on the tissue including but not limited to Xray as mentioned above, PET, MRI, Ultrasound, Spectroscopy, OCT, Xray diffraction, etc.

Figure 2:
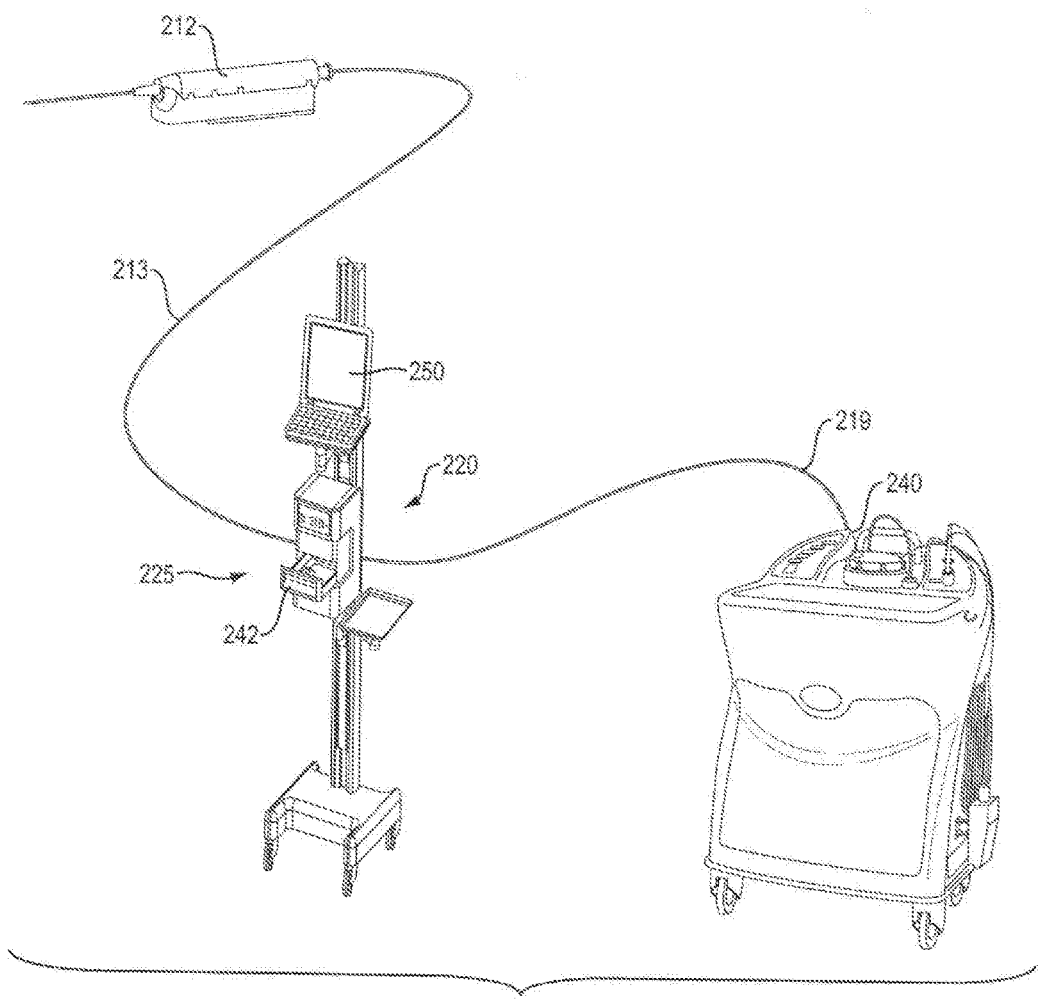
FIG. 2 illustrates an embodiment of the system of FIG. 1 for performing breast biopsy procedures.

FIG. 2 illustrates a biopsy suite embodiment of the system of FIG. 1. The biopsy suite includes a Radiography Specimen Cabinet (RSC) 220 coupled to a biopsy device 212. The biopsy device of 212 in one embodiment is a so-called Vacuum Assisted Breast Biopsy (VABB) device such as the Eviva® VABB device provided by Hologic, Inc., of Bedford Mass., although it is appreciated that other types of biopsy, tissue, fluid, or cell removal devices may be readily substituted herein without affecting the scope of the invention. The biopsy device 212 may be coupled to a console 240 via tubing 213, 219. The console 240 may provide sources of vacuum, pressure, and fluid (liquid and/or gas) during the biopsy procedure. One example of such a console is the ATEC® Pearl console, also provided by Hologic, Inc., although any form of a device capable of controlling cutter movement and optionally vacuum may be used.

The RSC includes x-ray imaging equipment for imaging an excised tissue sample in a viewing or "staging" area 225. After the biopsy sample is excised from the breast using the biopsy device 212, the sample is pulled through the tubing 213 to the staging area 225 by vacuum from console 240. A fluid such as saline may be used to lavage the breast cavity during excision, and to vent the core sample to facilitate transport to the RSC. In various embodiments which will be described below a specimen holder 242 may be disposed in the staging area 225 for delaying or stopping movement of the tissue sample through the staging area for at least a period of time sufficient to obtain an x-ray image of the tissue sample. In some embodiments the specimen holder 242 also functions as a tissue collection filter for collecting imaged tissue samples. In alternative embodiments a separate optional tissue collection filter may be used downstream relative to the specimen holder, e.g., in the RSC cabinet, in the console, or between the cabinet and console. A keyboard and/or touchscreen display 250 coupled to the RSC 220 may be used to accept input and provide information to the operator regarding imaging. For example, an image of the sample may be presented for viewing and classification.

Figure 3A:
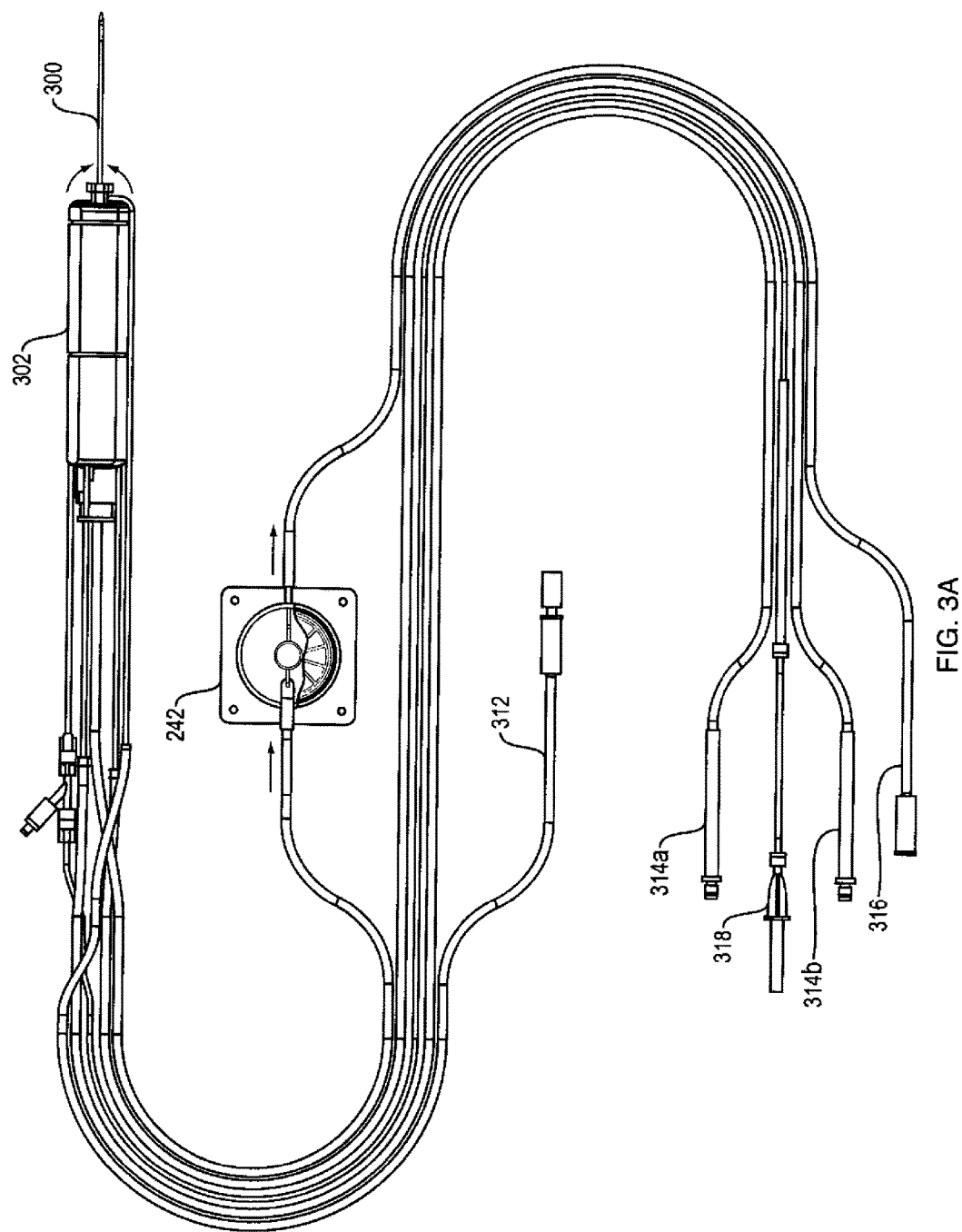
FIG. 3A illustrates a biopsy device according to the present invention in greater detail.

FIG. 3A illustrates an exemplary biopsy device in greater detail. The biopsy device includes a biopsy needle 300. The biopsy needle may be arranged as a tube within a tube. Such arrangements generally include an piercing cannula having a sharp distal tip and a cutting window or other opening proximal to the distal tip. The inner and/or outer move with respect to one another in order to sever any tissue in the cutting window. In the embodiment of FIG. 3A, the biopsy needle is coupled to a biopsy device 302. In various embodiments, the biopsy device may be configured for hand-held biopsies, or may be mounted to a support for stereotactic biopsies.

The biopsy device includes a plurality of inlet/outlet ports, through which are coupled a corresponding plurality of tubes. They may include a vacuum port coupled to vacuum tube 316, a saline port coupled to saline line 318 and a vent port coupled to vent line 312. Pneumatic ports, coupled to pneumatic lines 314*a* and 314*b*, may also be provided to control pneumatic type VABB devices, although they may not be required for biopsy devices which use other drive mechanisms such as electrical systems or drive cables.

Figure 3B:
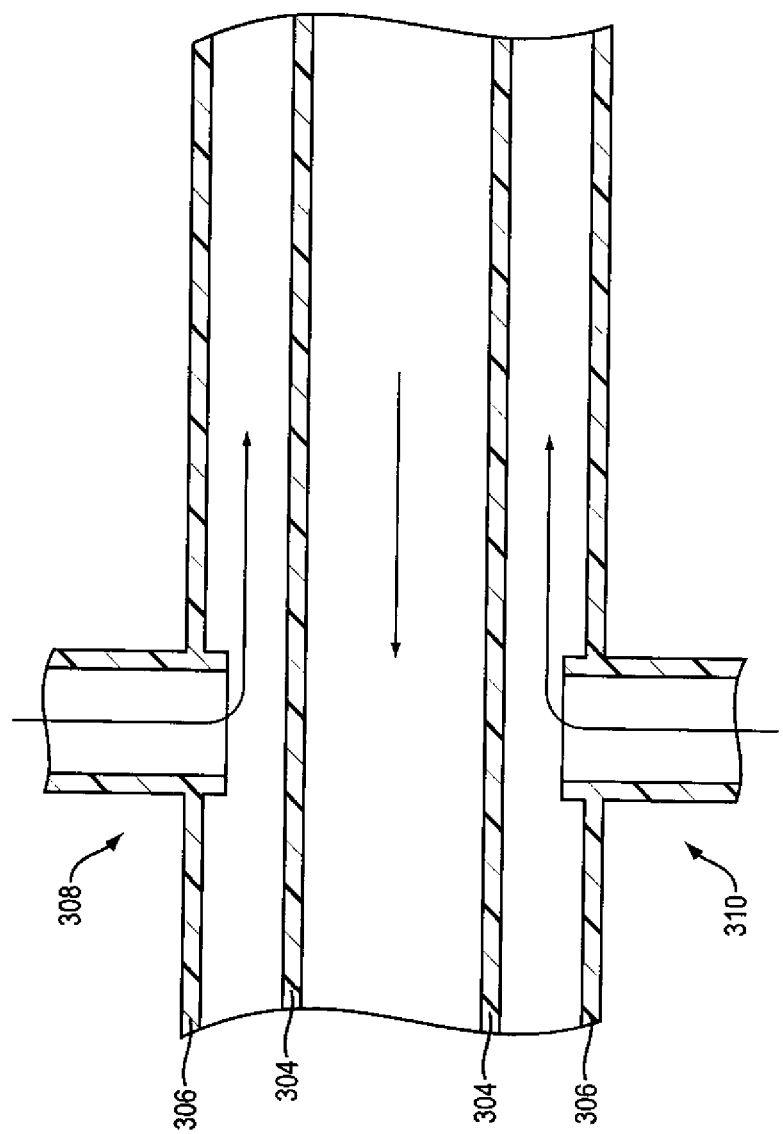
FIG. 3B is an expanded view of the cannula of the biopsy device of FIG. 3A.

FIG. 3B illustrates an exemplary placement of the saline port 308 and vent port 310, which extend through the walls 306 of the outer cannula of biopsy needle 300. Venting can be performed with fluid including but not limited to saline or air at a pressure above perfect vacuum (e.g. −28 inHg, −27 inHg, . . . 0 inHg, 20 inHg, and so on). Venting relieves the potential vacuum lock created between the core and the cavity, as the core is removed from the cavity. This facilitates easy removal of the core from the body. It is also recognized, that the tissue could also be removed without venting. During the biopsy, saline is applied through port 308 to lavage the biopsy cavity and vent the core. To enhance core transport speed it may be desirable to vent with air rather than saline. The optional vent port 310 is one possible feature for air venting. Alternatively, venting could be implemented by introducing air to the saline line and eliminating the need for a separate vent port 310. Alternatively, air or saline could be used alone through the saline port 308 to vent the core, and eliminating the need for the second vent port 310. Although it is not required to provide such a vent port, according to one aspect of the invention it is realized that venting the outer cannula with air in this manner greatly improves the speed of travel of the biopsy core through the inner cannula to the tissue specimen holder.

Referring to FIGS. 2, 3A and 3B, when used with the present invention, the vacuum source provided by the console pulls tissue into the cutting window, and as the inner cutter traverses past the cutting window, the tissue within the cutting window is severed from the patient to produce the biopsy sample, or biopsy 'core'. The biopsy sample is pulled through the inner cannula and through the tube 316 towards the console, and captured in the interim by the specimen holder 242. Controlled (non-constant) venting of the core using the system controlled vent line 312 expedites the movement of the core along the vacuum line 316 towards the specimen holder 242. Controlled venting is a process that controls when the vent line and/or saline line opens to the atmosphere or saline source. Thus, relieving the potential vacuum lock created between the core and the cavity, as the core is removed from the cavity. Controlled venting implies that the vent source is not always open to relieve this vacuum lock. However, it should be noted that venting might alternatively be constant and always open to relieve the vacuum lock.

Figure 3C:
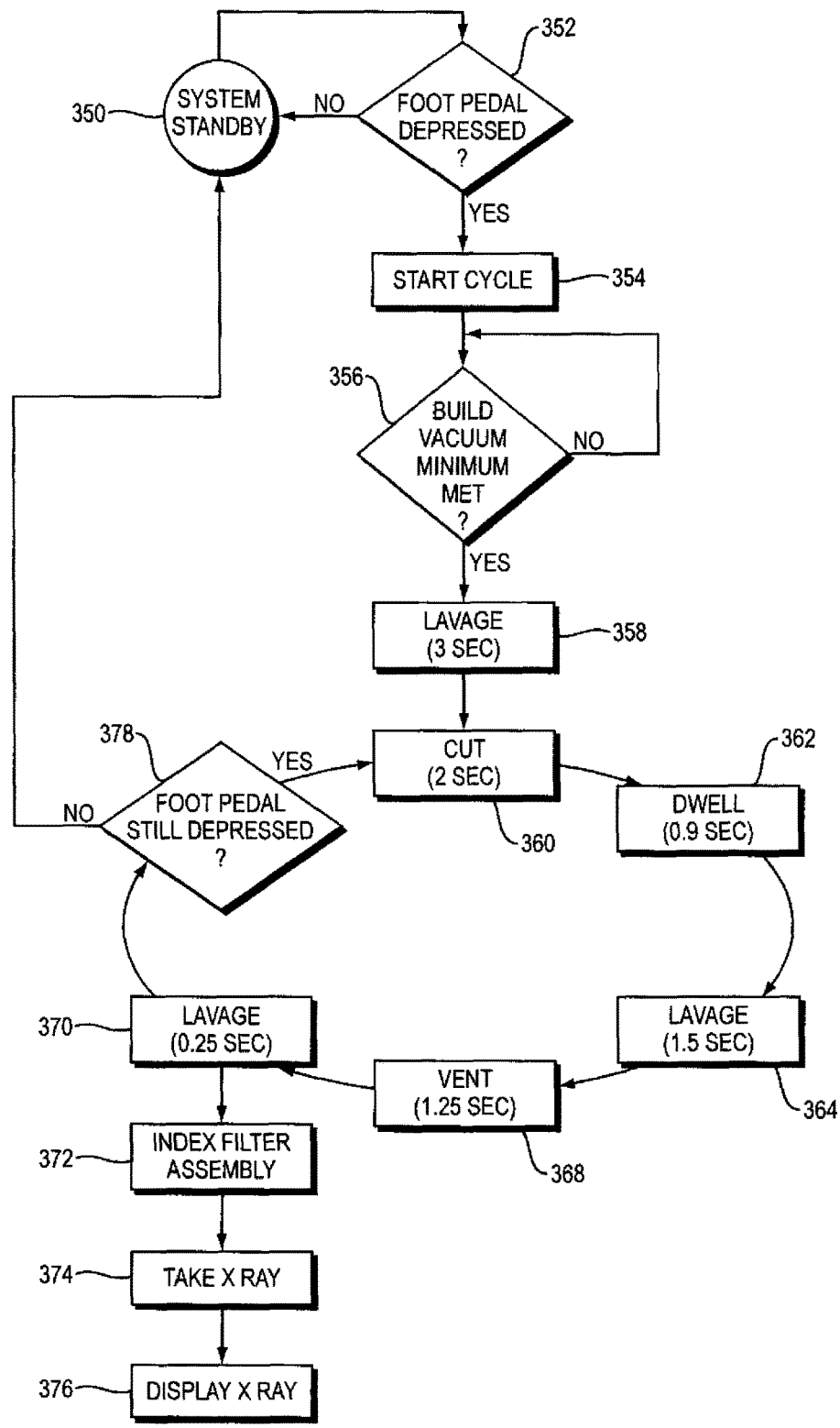
FIG. 3C is a flow diagram provided to illustrate exemplary steps in a process for in-line imaging of excised tissue according to principles of the present invention.

FIG. 3C is a flow diagram outlining an exemplary process for core collection using the biopsy device of the present invention. In one embodiment, each step within this process is automatically controlled in a timed sequence following sequence initiation, where sequence initiation may be caused by manual or other means. Other embodiments envision combinations of automation and manual intervention. In the process of FIG. 3C the depression of a foot pedal signals the start of each core acquisition. At step 350 the system is in standby mode prior to the initiation of the biopsy. At this point the cutting window is closed. First the biopsy needle is inserted into the appropriate location in the patient's breast. Then, at step 352 start of the biopsy is initiated, for example by depression of a foot pedal or other form of input. The biopsy cycle thus begins at step 354; at this point the vacuum pressure begins building while the biopsy cutting window is still closed (i.e., the cutter is advanced to a position such that it covers the biopsy cutting window). The saline and vent lines are also closed at this point.

At step 356 the minimum vacuum pressure is met. Once the minimum vacuum pressure is reached at step 356 the cutting window is opened and saline flows through saline line 318 (FIG. 3A) into the outer cannula 306 (FIG. 3B) via port 308 (FIG. 3B) and ultimately through the cutting window, lavaging the cavity at step 358. Thereafter the saline line is closed, and the inner cannula rotates and advances, extracting a core at step 360. At step 362 the cutting window remains closed during the dwell period, ensuring a complete cut of the sample. At step 364 both the saline line and cutting window are open, at which point saline is allowed to be pulled into the outer cannula to relieve the vacuum lock, and the increased vacuum draws the core tissue back through the inner cannula and handpiece towards the vacuum line. At step 368 the vent line is opened, allowing air to also be vented into the outer cannula, to expedite movement of the core to the specimen holder. At step 370 the vent line is closed, and the lavage of the cavity and the inner cannula continues.

During this lavage, the core advances into a location in the filter assembly. At step 372 the filter assembly is indexed. The indexing step rotates the specimen holder such that the core that was just received is now aligned with the x-ray source and detector and ready for analysis.

At step 374 an x-ray of the core is obtained and at step 376 the x-ray image is displayed to a medical professional. The image may be displayed at display 250 (FIG. 2), or on a workstation or other imaging device which is coupled to the RSC. In one embodiment, the display 250 includes a user interface which allows the medical professional to mark the image, where the mark may be a particular location in the image that is of interest, or just reference the fact that the image is of interest. As will be described in more detail below, the image that is displayed may be a raw image, or may be an image which is processed using computer assisted detection (CAD) software to highlight regions of interest within the image. The display may include zoom capabilities or other methods for modifying the image, and storing the modified image, along with or in place of the original image, for later review. This process may continue for example until all desired cores have been harvested or until the specimen holder 242 (FIG. 2) is full, or the user wishes to stop taking samples. The specimen holder or a filter element therein is then replaced, emptied or otherwise prepared, although additional cores might also be captured even if the filter is full, e.g., multiple cores would occupy a single chamber.

In one embodiment of the invention, a location, or each chamber, within the specimen holder can be correlated to an image of that particular location or chamber, e.g. the specimen holder has unique identifiers that are visible in the radiograph and by the naked eye. Relating a location within the specimen holder to an image facilitates later review of the biopsy results; that is a medical professional can more quickly identify the particular core which displayed a calcification. According to a further aspect of the invention, the location within the specimen holder is further correlated to a particular rotational angle of the cutting window of the biopsy needle. Many biopsy devices can be rotated or include a rotatable outer cannula or device which permits extraction of tissue in a 360 degree circumference around the insertion location of the device. The ability to relate a particular location in the specimen holder to an angular rotation of the biopsy window of the device provides additional information regarding where, within the breast, calcifications were obtained.

Figure 4A:
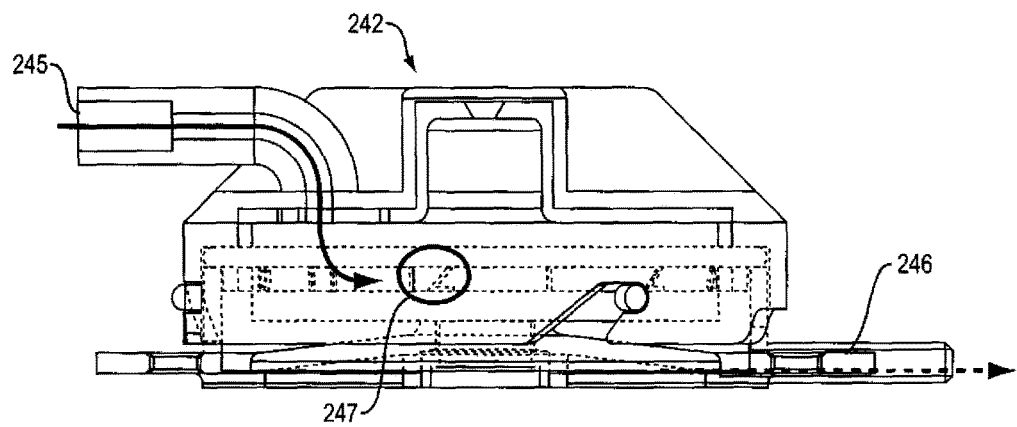
FIGS. 4A and 4B are perspective diagrams illustrating an exemplary specimen holder of the present invention.
Figure 4B:
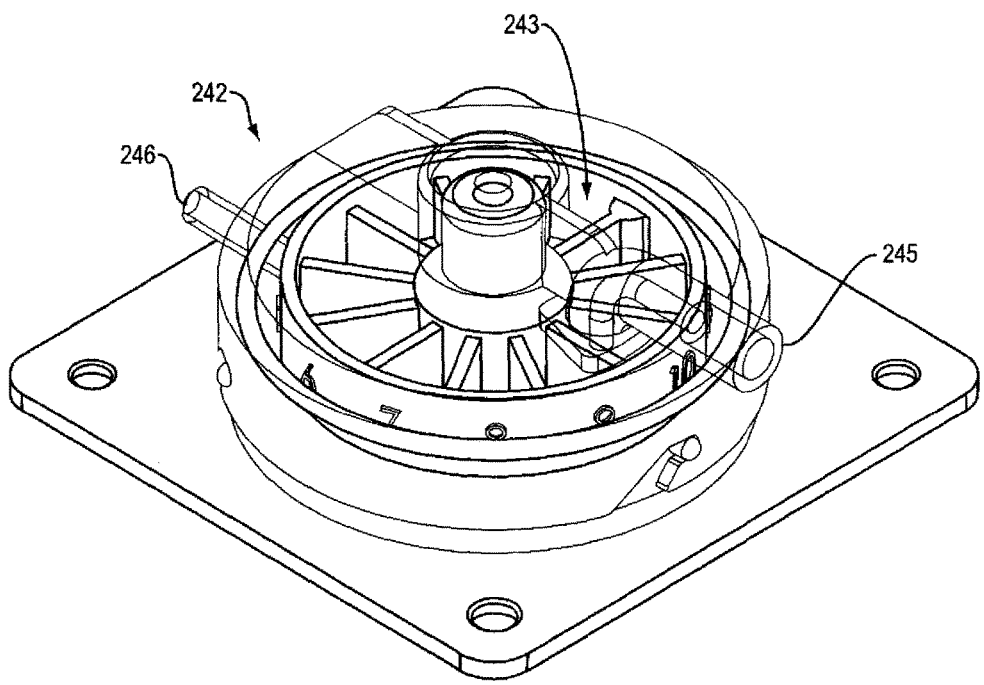

Referring briefly to FIGS. 4A and 4B, a diagram of a representative specimen holder 242 of the present invention is shown to include a plurality of tissue accepting slots 243, an inlet port 245 and an outlet port 246. This so-called carousel type specimen holder 242 is preferably formed from a radiolucent material. The inlet port 245 is coupled to a first portion of the vacuum line (i.e., an upstream portion) and the outlet port 246 is coupled to a second portion of the vacuum line. During core collection, tissue is forwarded through the vacuum line, into the inlet port, and captured in the individual slots. Excess saline and bio-fluid flows through the carousel of the specimen holder to outlet port 246, and out towards a collection filter in the console. In one embodiment the x-ray source and detector are aligned with a specimen holder slot immediately adjacent to the inlet port. The filter is then indexed after receiving the core, to align the core with the x-ray source and detector. Alternatively, the analysis or imaging could occur over any slot or image the entire specimen holder. Alternatively, the core may be presented for imaging using other means. As shown in FIG. 4A each slot is assigned a unique identifier 247. In the illustrated example the unique identifier is a number for the slot, although other identifiers such as letters, barcodes, raised nubs, etc may be readily substituted therefore. More specifically, uniquely marking the slots, e.g., with radio-opaque markings, helps to match samples with associated images, provided such markings do not interfere with the x-ray.

In one embodiment the system is arranged so that the initial core is always captured in a pre-identified slot. The specimen holder may be designed with a feature that facilitates the alignment of the specimen holder in a particular position for the start of a biopsy. The alignment mechanism may be something as simple as a tab or slot, or may use other means, such as magnetic orientation or the like to ensure that the appropriate slot is in the proper location during the start of a biopsy. A Hall effect or other device can be used to orient the carousel relative to a home position, e.g., where the initial compartment is aligned with the inlet port.

A belt, gear, chain, or any means to transfer rotation is coupled to either a central axle or the outside surface of the carousel of the specimen holder. A motor drives the belt, gear, chain, or other to rotate the carousel. The belt, gear, chain, or other may be formed of radiolucent material so as not to interfere with image acquisition, and/or may be positioned such that it is not aligned with the x-ray source and detector. Direct drive and other systems could alternately be used. The filter base and/or sidewalls may be mesh or other permeable material to facilitate draining bio-fluids away from the captured samples while still preventing the captured samples from exiting through the outlet port. The x-ray or radiograph of the specimen is taken and presented to the user. There could be one single radiograph or multiple. For example, a single radiograph could be taken of the entire specimen holder and capture images of all cores at once. Or, a radiograph of each individual chamber could be taken and presented to the user. In either embodiment, the radiograph may be labeled to correlate with the unique labeling on the filter. This can be accomplished using radiopaque markings on the filter that can be seen by the naked eye and that also appear on the radiograph, e.g. radiopaque ink to label each chamber numerically, alphanumerically, symbols, or other means. This could also be accomplished by labeling the filter with a unique label visible to the naked eye, and then having the unique filter chambers identifiable by the RSC (e.g. filter uniquely labeled alphanumerically, when installed into the RSC it is able to determine the position of each unique chamber and track it as it is indexed and then label it as shown in FIG. 8b—"A", "B", and "C").

It should be noted that although automated systems for specimen capture and analysis are described herein, manual steps could be implemented to facilitate either or both specimen capture and analysis. For example, the specimens or specimen containers could be manually moved into the analysis device. Similarly, push button controls could be used to begin analysis or other steps.

Figure 5A:
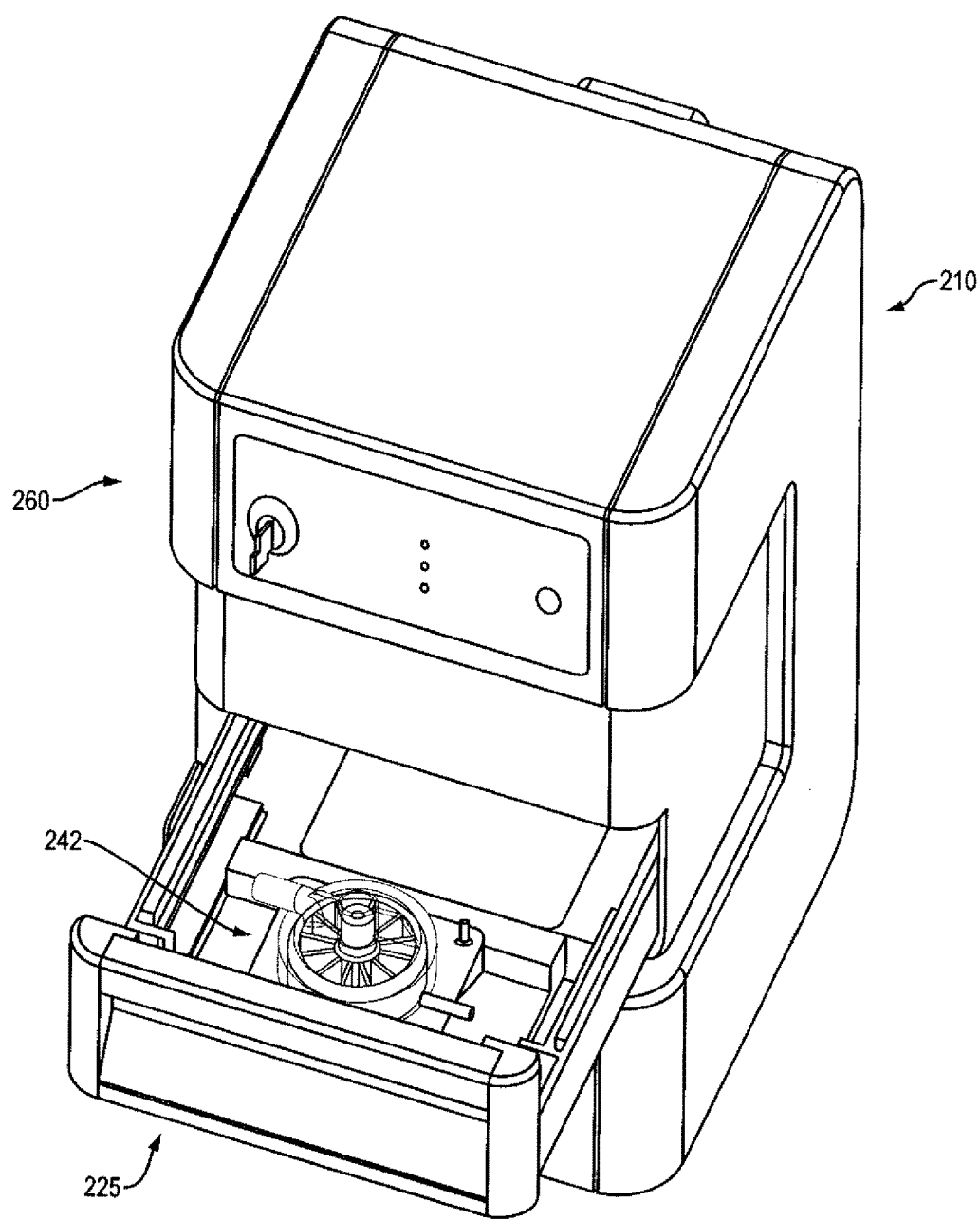

Once the biopsy has been completed, the medical professional can remove the filter or specimen holder from the specimen tray. FIG. 5A is a view of the RSC showing the specimen holder in an open position. As shown in FIG. 5B, the operator may remove the cover 291 of the specimen holder in order to gain access to an inner filter 293 or retaining member which is removed from the specimen holder The filter 293 contains all of the cores. The filter 293 can be capped or covered, and placed into a specimen jar filled with formalin. Alternatively, the specimen holder and integral filter could be designed to be removed from the RSC, filled with formalin or other fixative, then capped to double as specimen holder and specimen jar. Although saline and bodily fluids are transferred through the specimen holder during the biopsy process, the tubing and specimen holder are water tight in arrangement, and therefore no hazardous waste remains in the RSC following the biopsy process. The user has the option to review the radiograph(s) and determine which cores have calcifications. For example, FIG. 8b shows three radiographs. The user would review the three radiographs and determine which cores have calcifications. The user can now communicate to the pathologist which cores have calcifications, e.g. cores in chambers A, and C have calcifications. Specimen jars and labels could be customized to facilitate this communication, e.g. labels on specimen jars with "Cores with Calcifications are located in chambers—(fill in the blank)." The cores are ready for transport to the pathology lab for further analysis. Another carousel or retaining member can be placed in the specimen holder in order to prepare for a subsequent procedure. This describes a new system that provides near real time feedback (e.g. radiograph or other analysis means) to the user during the procedure, and enables the user to communicate to the pathologist which tissue specimen may have an abnormality (e.g. calcification if using radiograph, or abnormal area using other analysis means).

Figure 6:
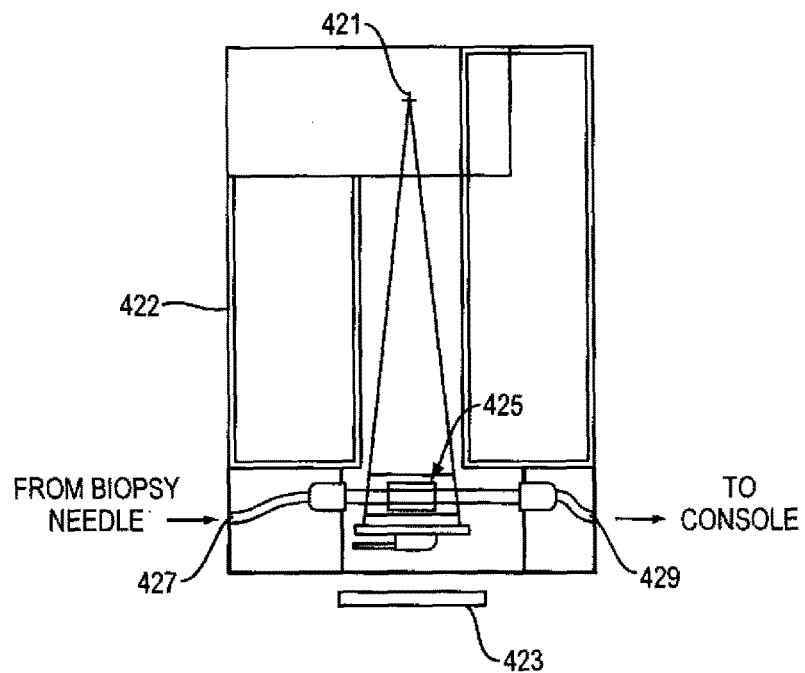
FIGS. 6 and 7 illustrate various embodiments of a RSC, each with different arrangements of the x-ray source and detector.
Figure 7:
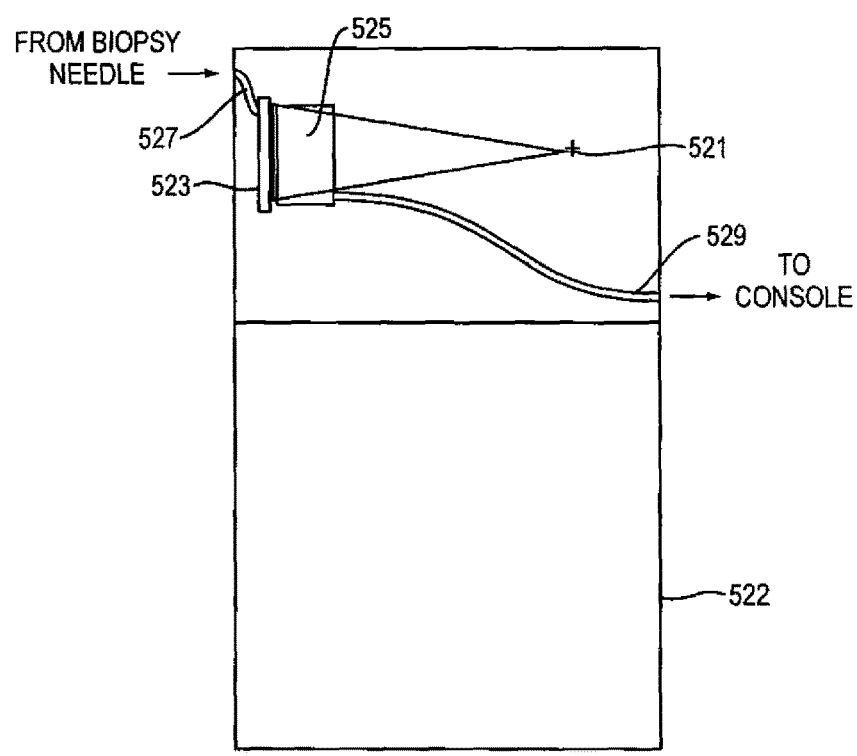

FIGS. 6 and 7 illustrate embodiments of the RSC in greater detail. Some features are common to both embodiments. For example, input ports 427, 527 represent a group of ports (such as those shown in FIG. 3A) that link the RSC to the biopsy device (212, FIG. 2) and output ports 429, 529 represent the group of ports (such as those shown in FIG. 3A) that link the RSC to the vacuum console (240, FIG. 2). The ports may be configured to allow for easy connection and disconnection of the tubing such that the biopsy needle can be connected and disconnected to and from the RSC, and would also allow the entire specimen holder to be removed from the biopsy device. Such a modular configuration facilitates mobility and advantageously allows use of different excision and analysis tools and vacuum sources. Both embodiments include an x-ray source 421, 521 such as a micro focus X-ray tube, a collimator (not shown), a x-ray detector 423, 523, an exposure timer (not shown) and a staging area 425, 525. According to one aspect of the invention, the detector is a direct digital detector, providing high quality images for rapid specimen verification. Both embodiments are also enclosed in cabinets 422, 522 having sufficient shielding to isolate the x-ray energy. As discussed above, an interface with I/O devices such as a keyboard and display 450, 550 may be integrated with or otherwise coupled to the RSC. Wheels may be attached to the cabinets to facilitate mobility.

A principal difference between the embodiments of FIGS. 6 and 7 is the relative orientation of the detectors 423, 523 relative to the x-ray sources 421, 521. In the embodiment of FIG. 6, the x-ray source 421 and x-ray detector 423 are positioned for horizontal imaging because the x-ray source directs energy vertically within the cabinet towards the detector. It will be appreciated that the x-ray source could be positioned either above or below the specimen holder. In the embodiment of FIG. 7, the x-ray source 521 and x-ray detector 523 are positioned for vertical imaging because the x-ray source directs energy horizontally within the cabinet towards the detector (note that the x-ray source could be on the left or right). Other orientations might also be used. Orientation of the x-ray source and detector is a matter of design choice which may depend upon factors such as cabinet dimension constraints, port location and bend radius of the tubing used to move the sample within the cabinet. Consequently, the present invention is not limited to use with a RSC having any particular x-ray source/detector orientation.

Figure 8A:
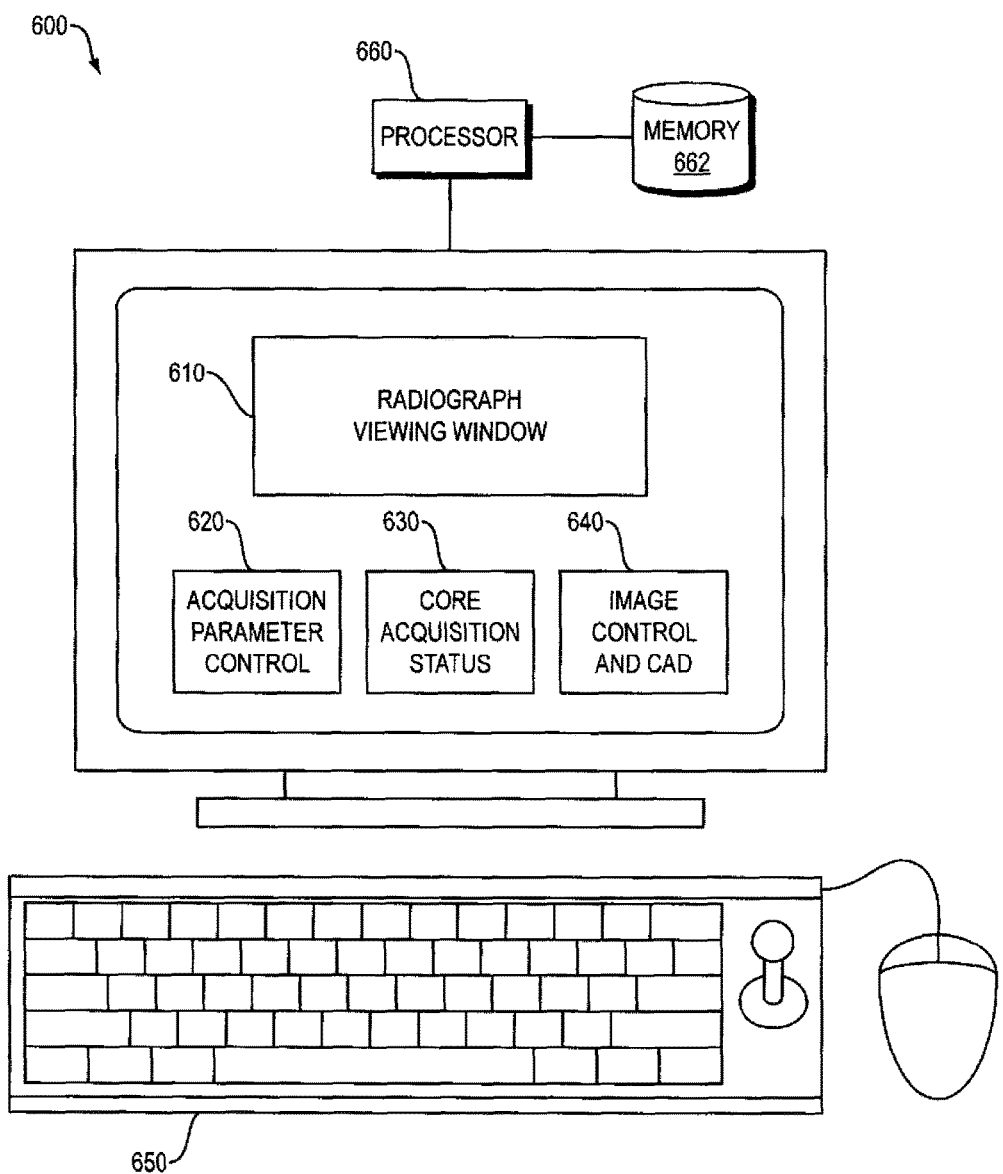
FIG. 8A illustrates an exemplary display and associated interface features in block diagram form.
Figure 8B:
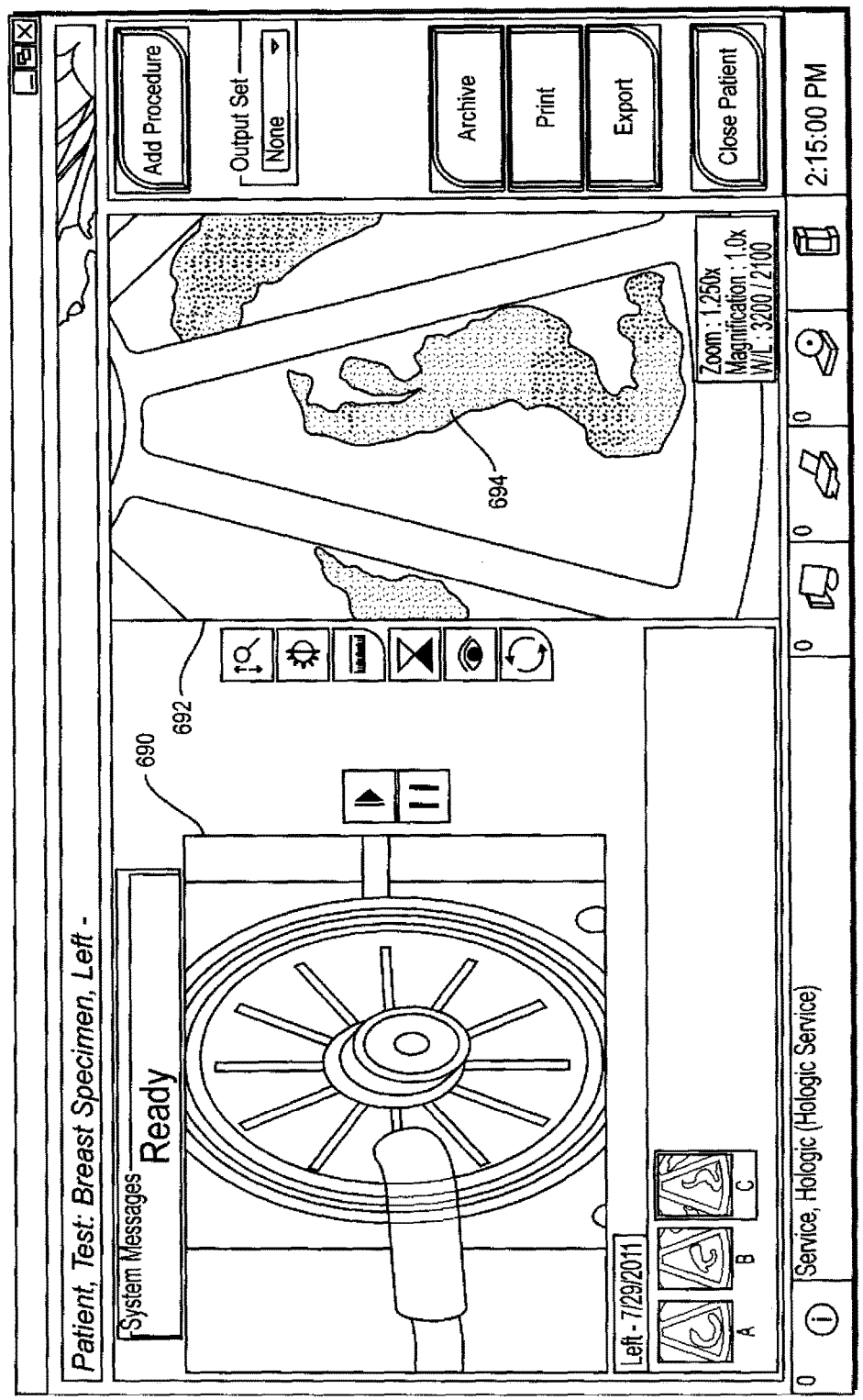
FIG. 8B illustrates an exemplary interface screenshot.

FIG. 8A illustrates aspects of a RSC display 600 and associated interface features in block diagram form. The display 600 may include a radiograph viewing window 610 for providing relatively instantaneous acquisition information to the operator. A keyboard 650, which may include a mouse, joystick, or other manual controllers, may be used to manipulate the acquired image. A touch screen might also, or alternatively, be used. A pull-down menu or other interface 620 may be provided to enable the operator to customize acquisition parameters such as exposure time, kV, AEC parameters, etc. In addition, a status window 630 may be provided. The status window may include information such as the number of samples acquired and number of calcifications detected. In one embodiment, the interface may provide an audible or visual indication to the operator in regards to whether the current radiograph or prior radiograph contains calcifications. The indication may include, for example, ringing a bell, displaying a pop-up window, checkmarks or borders on thumbnails, circles around calcifications on radiographic images, or displaying some other visual indicator. As discussed previously, it is further envisioned that the display or user interface could also include controls which permit a user to dynamically process an image, such processing ability including the ability to apply different filters to the image, uses CAD algorithms to process the image, resize the image, mark the image, mark regions in the image, etc. It is further envisioned that the display may include thereon a 'bucket' which would enable the user to drag and drop images of interest to the medical professional, allowing the professional to dynamically manage their workflow.

Referring to FIG. 8B, the display shows a picture or live video 690 of the specimen holder and a radiograph 692 of a specific core sample in the specimen holder. The video may be presented in real-time such that the operator can see what is currently happening within the staging area. The radiograph may be slightly delayed or real time such as fluoroscopy. The operator may thus be able to view the video and imaged calcifications 694 in real time or near real time.

Computing resources such as a processor 660 and memory 662 are coupled between the display 600 and detector. Software which is stored in the memory (a non-transitory computer readable medium) is included for processing image data associated with tissue samples, for example including the software allowing the operator and others to view and manipulate the images, perform other image processing, data collection, and data management functions. As mentioned above, the software may include one or more image control and Computer Assisted Detection (CAD) programs with a display feature 640 for highlighting calcifications, abnormalities or other regions of interest in images, and representing the identified regions of interest to the operator, e.g., a surgeon or radiologist. The software may cause the processor and display to provide indications to the operator regarding the presence and/or absence of calcifications in an image acquired by the RSC, including visual or audio feedback which indicates detection of calcifications or the location of detected calcifications. The display, computing resources and other IO devices may be configured to enable the surgeon/radiologist to customize one or more x-ray acquisition parameters, including voltage, magnification, duration, etc.

Figure 9A:
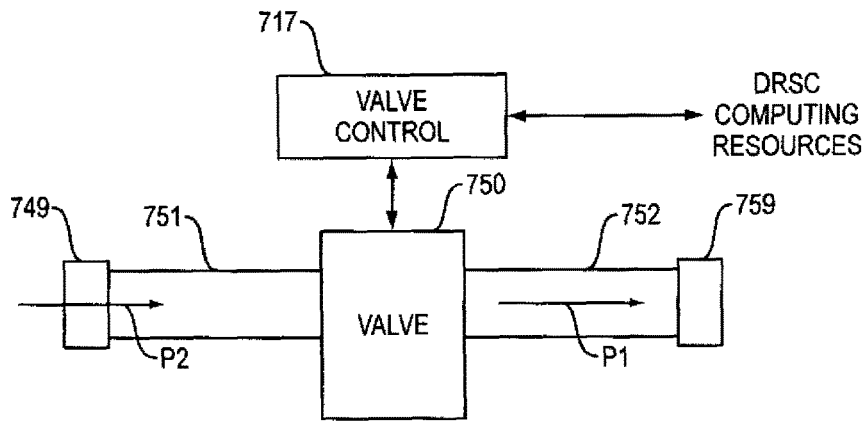
FIGS. 9A through 9C illustrate an alternate embodiment of the specimen holder which is disposed in the staging area for facilitating imaging of tissue samples.
Figure 9B:
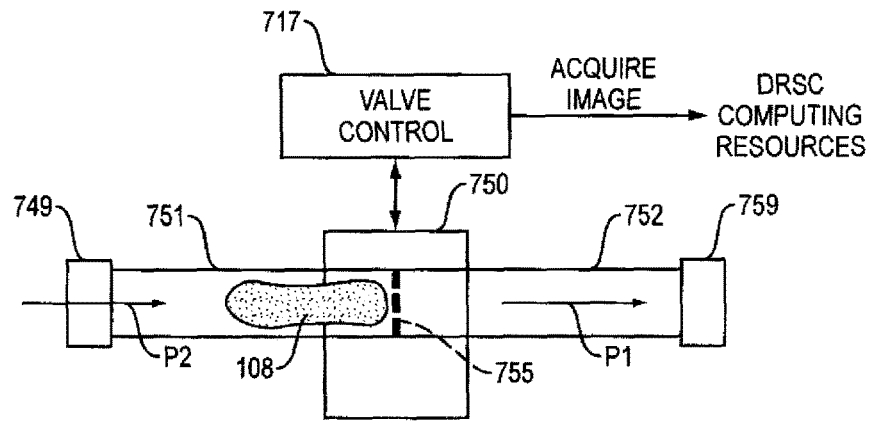
Figure 9C:
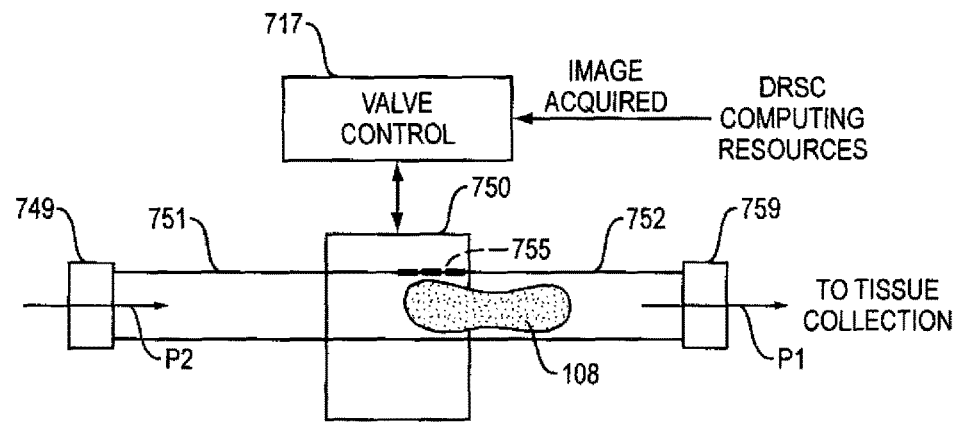

FIGS. 9A through 9C illustrate an alternate embodiment of the specimen holder 242 (FIG. 2) which is disposed in the staging area for facilitating imaging of tissue samples. The illustrated specimen holder includes a valve 750 coupled between an inflow line 751 and an outflow line 752. The valve is operative to temporarily stop a tissue sample 108. Optional connectors 749 and 759 are coupled to the inflow and outflow lines, respectively. Luer taper or similar friction fit connectors may be used, but the invention is not limited to any particular type of connector. In this embodiment the valve 750 may be a normally closed (NC) type which is adapted to permit fluid flow in both the open and closed states. In particular, the valve is adapted to function as a filter when in the closed state. This may be accomplished by replacing material from a portion of the valve that would normally block fluid flow in the closed state with a mesh type screen. The screen is characterized by a gauge selected to permit fluid flow but prevent passage of the tissue sample. Any type of valve might be utilized.

The valve 750 is actuated in response to a valve control device 717. The valve control device can include mechanical, electrical and electronic elements for exerting control over the valve. In particular, the valve control device is operative to cause the valve to change state, i.e., open or close. The valve control device may operate in response to a trigger condition, e.g., motion detection by a motion sensor associated with the valve control device 717, timing based on the console or cycle, or a manual trigger. Motion could initially be detected from the presence or approach of a tissue sample in the inflow line 751. Alternatively, or additionally, the trigger condition may include the detection of a pressure differential between the inflow line 751 pressure P2 and the outflow line 752 pressure P1 using pressure transducers associated with the valve control device 717. The lack of a difference in pressure is indicative of the absence of a sample, and a difference in pressure is indicative of the presence or approach of a tissue sample in the inflow line 751. The valve could alternatively be actuated by console input, e.g., closed for most of cycle to capture and image the core, and open for a short interval to release the core.

The trigger condition may be used to initiate a time sequence of events including the acquisition of an x-ray image by the RSC followed by the opening of valve 750 to release the tissue sample 108 into the outflow line 752. For example, FIG. 9B illustrates a gate type normally closed (NC) filter valve gate 755 in a closed position. Fluid flows through a mesh in the valve gate 755 in the closed position. As the tissue sample 108 is received in the inflow line 751, its movement is impeded by the mesh of valve gate 755. Fluid pressure P2 increases behind the tissue sample in the inlet line 751 because the sample impedes fluid flow through the mesh portion of the valve gate 755. The presence of the tissue sample is detected by the valve control as already described above, e.g., based on pressure differential (P2>P1). In response, the valve control device prompts the RSC computing resources to acquire an x-ray image of the captured sample. A timer or return signal indicates to the valve control device that the image has been captured. In response, as shown in FIG. 9C, the valve gate 755 is opened by the valve control device 717. Back pressure in the inflow tube then flushes the sample 108 into the outflow tube 752 toward the console or other tissue collection device. The resulting lack of a pressure differential between the inflow line 751 and outflow line 752 due to removal of the sample is then detected by the valve control device, which prompts the valve gate to close in response. Alternatively, motion detection, console output, manual trigger, pressure monitoring, etc and any combination of could be used to initiate the timed sequence of events described above. Moreover, tissue capture, imaging, and valve operation can be controlled based on sensing presence of tissue or timing of console/cycle.

Figure 10A:
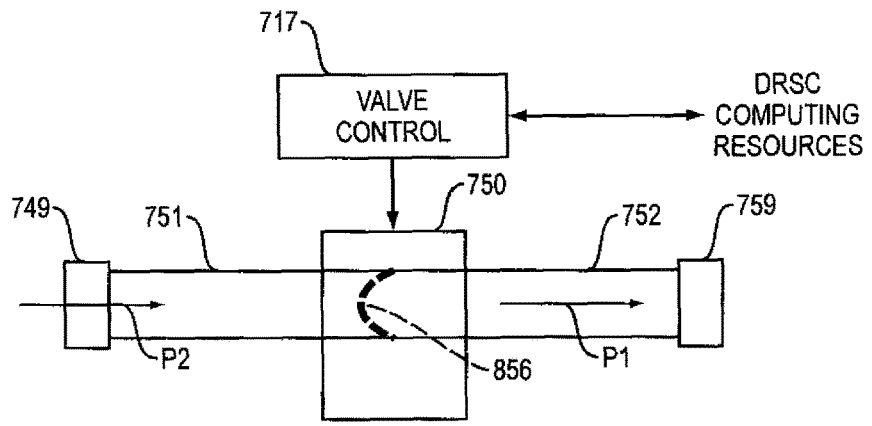
FIGS. 10A through 10C illustrate variations of the specimen holder of FIGS. 9A through 9C with various other types of valves.
Figure 10B:
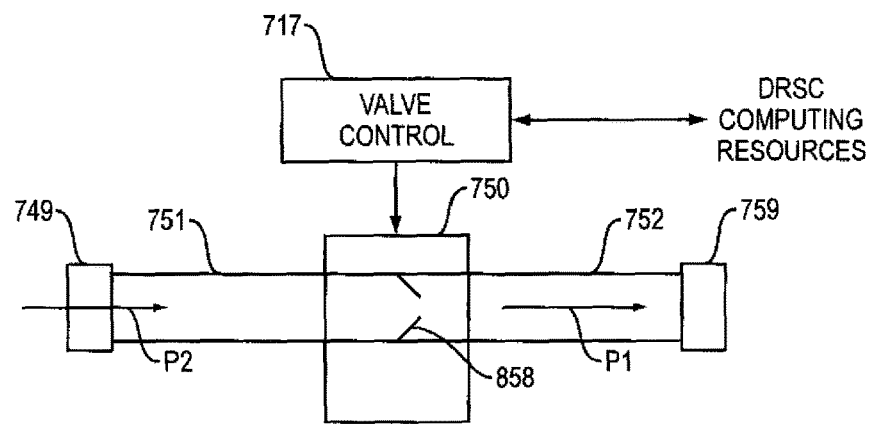
Figure 10C:
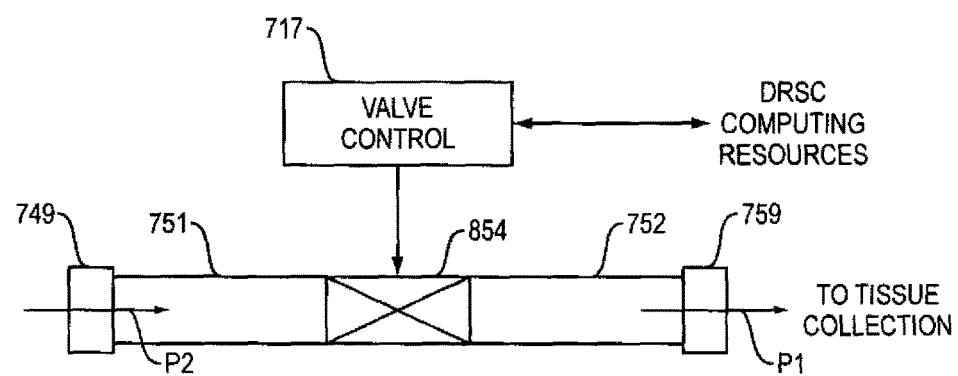

FIGS. 10A through 10C illustrate variations of the specimen holder of FIGS. 7A through 7C with various other types of valves, including a ball valve 856, a paired gate valve 858 and a solenoid valve 854. These valves may be controlled to open following detection of the presence or approach of the tissue sample as described above. Alternative valves may include, but are not limited to, a gate valve, butterfly valve, diaphragm valve, solenoid valve, and pinch valve.

Figure 11A:
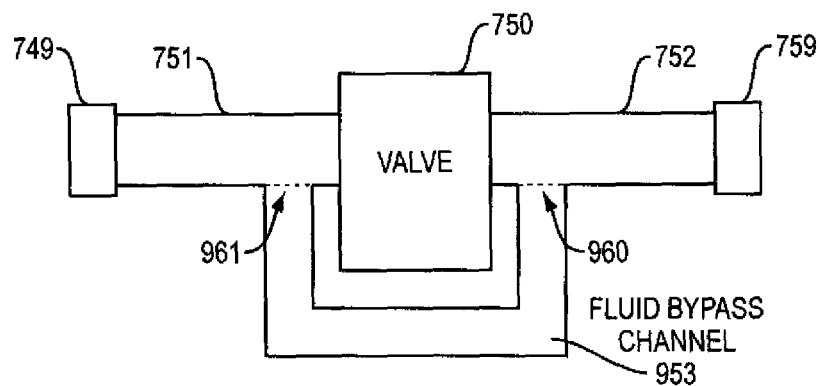
FIG. 11A illustrates an alternative embodiment the specimen holder including one or more bypass channels for permitting the passage of fluids around the valve.

Referring now to FIG. 11A, in an alternative embodiment the specimen holder includes one or more bypass channels 953 for permitting the passage of fluids around the valve 750. One benefit of the bypass channel is avoiding cutoff of vacuum to the biopsy device and movement of saline and cores when a core or cores are captured against a filter. Further, in this alternative embodiment the valve fluid flow in a closed state as the valve could be made of a mesh type of filter. The fluid bypass channel 953 is coupled between the inflow line 751 and the outflow line 752 to allow fluid to bypass once a core has been capture by the valve and has obstructed flow through the valve. In this condition, flow through the bypass will increase and pressure will rise in the bypass. The pressure could be monitored to determine when a core has been captured by the valve. Mesh filters 960 and 961 are disposed across connecting openings between the bypass channel and inflow and outflow lines to prevent biopsied tissue from entering the fluid bypass channel 953.

Figure 11B:
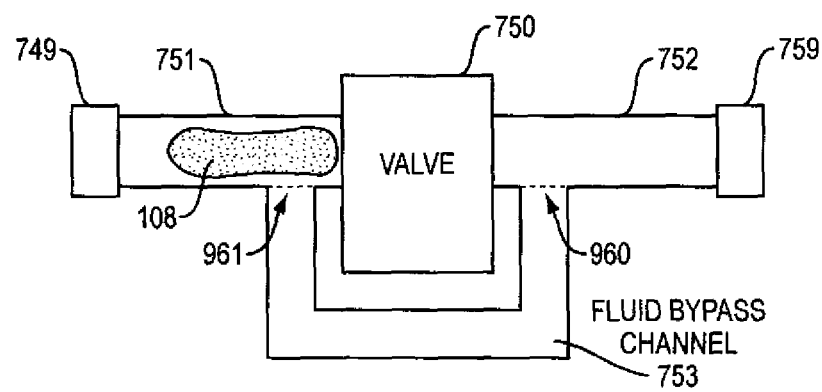
FIGS. 11B and 11C illustrate operation of the specimen holder of FIG. 11A.
Figure 11C:
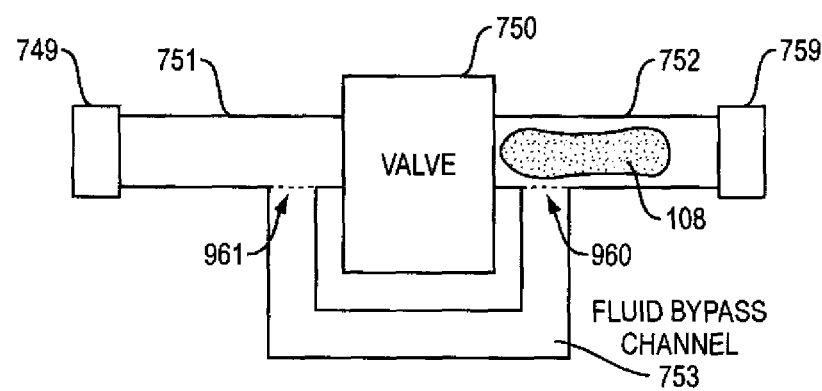

Operation of the specimen holder is shown in FIGS. 11B and 11C. FIG. 11B illustrates a tissue sample 108 being captured against the valve 750, which is closed. The captured core sample blocks flow through the valve and increases flow and pressure through the bypass line. A valve control and pressure transducers may be used to detect the presence of the tissue sample as already described above. A timer or motion detector might alternatively or additionally be used. Regardless of which technique is used to detect the presence of the tissue sample, the image is then acquired and the valve is opened to flush the imaged sample. FIG. 11C illustrates the imaged tissue sample moving through the open valve into the outflow line. When the elevated pressure is no longer detected the valve control prompts the valve to close. A timer or motion detector might alternatively or additionally be used.

Figure 11D:
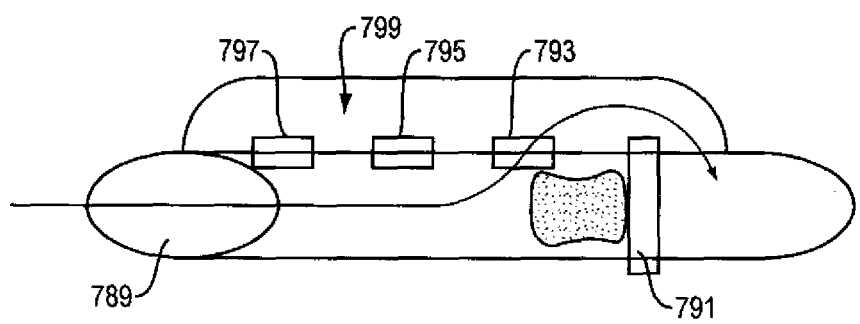
FIG. 11d illustrates a variant in which a filter is placed in a main channel and a series of filters allow fluid to flow into a bypass channel.

FIG. 11d illustrates a variant in which a filter 791 is placed in a main channel 789 and a series of filters 793, 795, 797 allow fluid to flow into a bypass channel 799. Filter 791 may have greater unobstructed flow capacity than filters 793-797, and filters 793-797 may be arranged in order of diminishing unobstructed flow capacity such that a tissue sample proceeds downstream without being captured against an upstream filter, e.g., because greater force moves the sample toward the downstream filter. As such, cores are captured and stored in series in the main channel 789. All of the cores can be imaged together, or the linear arrangement of cores could be moved under an analysis unit and analyzed section by section.

Figure 12A:
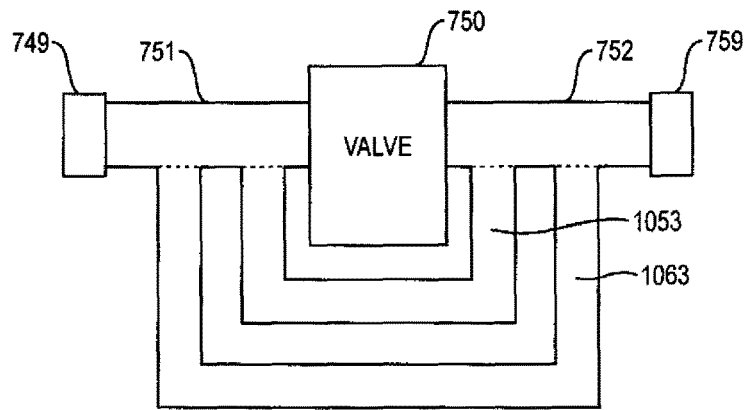
FIG. 12a illustrates another alternative embodiment of the specimen holder.
Figure 12B:
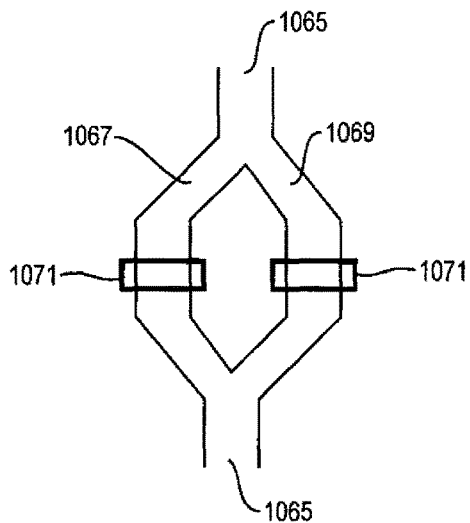
FIGS. 12b and 12c illustrates variants in which a main channel branches into two subchannels.
Figure 12C:
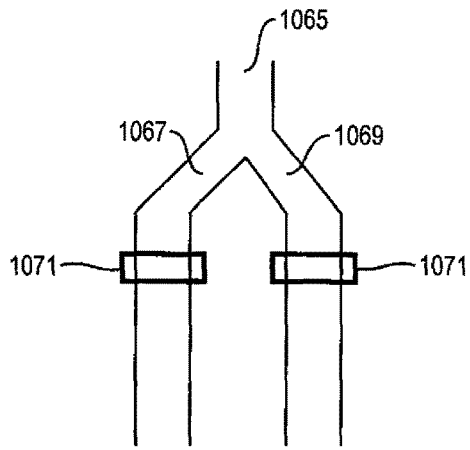

FIG. 12a illustrates another alternative embodiment of the specimen holder. The illustrated embodiment includes multiple fluid bypass channels 1053 and 1063. FIGS. 12b and 12c illustrate variants in which a main channel 1065 branches into two subchannels 1067, 1069. The subchannels may or may not reconnect and reform the main channel. Each subchannel includes a valve 1071 with a filter that allows fluid to pass when the valve is closed. Initially, a tissue sample will enter either the first subchannel 1067 or the second subchannel 1069, lodging against the closed valve. The sample impedes the flow of fluid through the valve against which it is lodged so a second tissue sample is directed by fluid flow into the other subchannel. The first captured tissue sample is then released by opening the valve, and a third tissue sample is directed into the free subchannel because the flow of fluid through the valve in the other subchannel is impeded by the second tissue sample. Hence, tissue samples are alternatingly directed into different subchannels where they may be analyzed prior to being released.

Figure 13A:
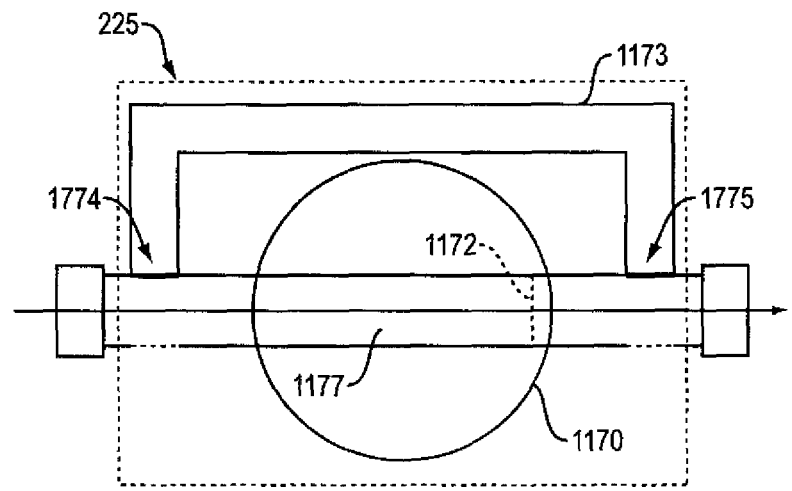
FIGS. 13A through 13D illustrate another alternative embodiment of the specimen holder.
Figure 13B:
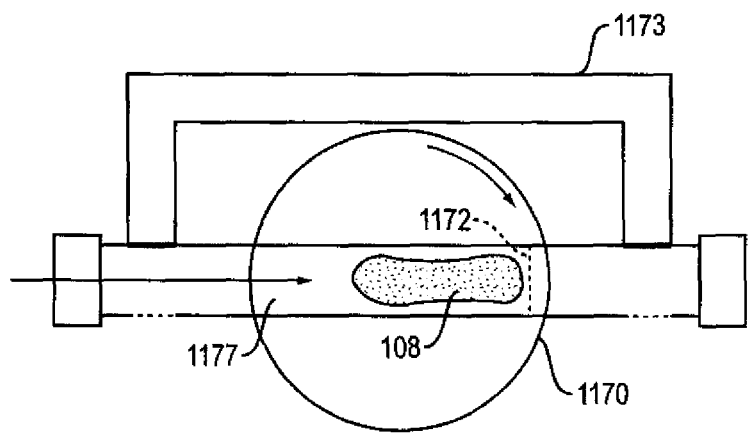
Figure 13C:
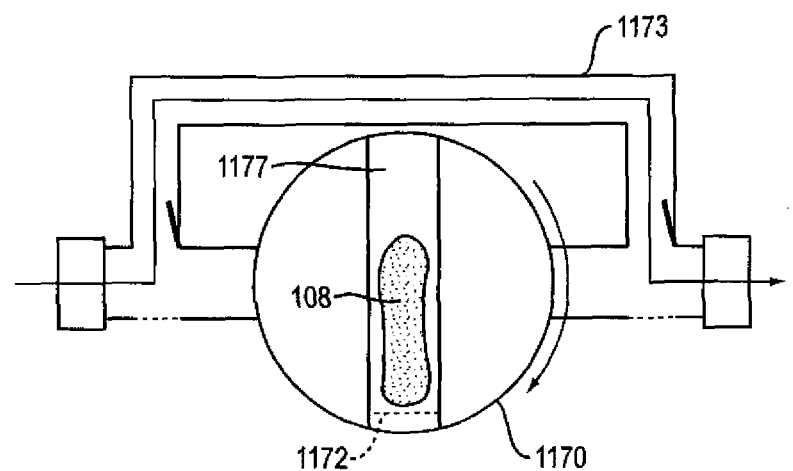
Figure 13D:
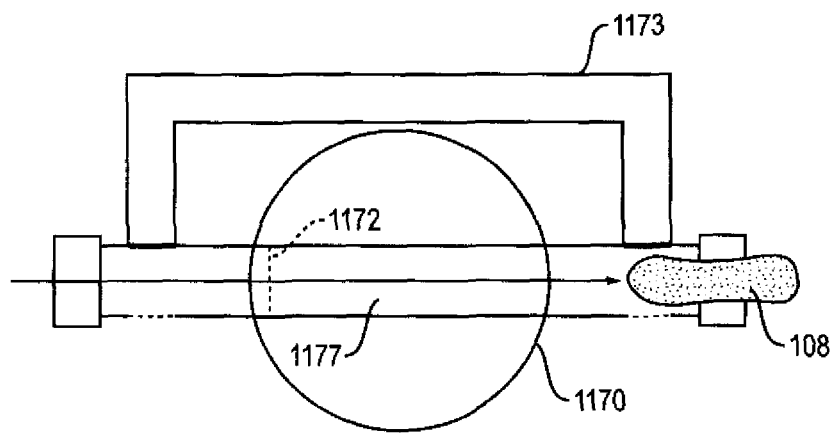

FIGS. 13A through 13D illustrate another alternative embodiment of the specimen holder. In this embodiment a rotatable tissue sample positioning mechanism 1170 with an interior channel 1177 and a filter 1172 are used to temporarily capture the tissue sample for imaging. The positioning mechanism 1170 may include a modified ball valve. An optional fluid bypass channel 1173 may be coupled to inflow and outflow lines via optional pressure sensitive valves 1174, 1175 and optional filters disposed across connecting openings between the bypass channel and inflow and outflow lines. With the pressure sensitive valves 1174, 1175 closed, the tissue sample 108 from the biopsy needle is pulled through the inflow line into the interior channel until it is stopped by the filter 1172, as specifically shown in FIG. 13B. Pressure in the inflow line tends to increase due to the sample impeding flow of fluid through the filter. The presence of the tissue sample may be detected using motion detection or pressure differential mechanisms similar to those described above. In response to detection of the presence of the sample the x-ray equipment is prompted to image the sample. The sample may be imaged with the positioning mechanism oriented as shown in FIG. 13B. Alternatively, the positioning mechanism is rotated ninety degrees (or some other amount) to move the sample into a desired imaging position as shown in FIG. 13C. The resulting increase in pressure is detected by valve 1174, which opens in response. Valve 1175 subsequently opens in response to a pressure increase following opening of valve 1174. Once the sample has been imaged the core positioning mechanism is rotated, e.g., a further ninety degrees, so that the filter of the interior channel is upstream relative to the sample, e.g., proximate to the inflow line. When the interior channel is again aligned with the inflow line the flow of fluid through the interior channel moves the sample into the outflow line as shown in FIG. 13D. Also, the decrease in pressure causes valves 1174 and 1175 to close. When the sample is no longer detected as being present the sample holder is reset by rotating the positioning mechanism back into the position shown in FIG. 13B. Alternatively, the filter might be positioned such that a subsequent sample can be captured with the positioning mechanism in the position which released the previous sample, e.g., using a filter disposed at the center of the interior channel. A variety of other positioning mechanisms which detect the presence of the sample and respond by sliding or otherwise moving the interior channel along an x, y and/or z axis into a desired position are contemplated herein and are therefore within the scope of this invention.

The specimen holder variants described above in which a channel is divided into multiple channels can be implemented in embodiments where channels reconnect, remain separate, or some combination thereof, e.g., some reconnect and some remain separate. Further, the specimen holder variants described above could be placed in series or parallel configurations in the staging area such that multiple specimens could be imaged simultaneously. Furthermore, the RSC could include multiple staging areas. It is also envisioned that a single specimen holder could capture multiple samples for simultaneous imaging (e.g. tissue filter with a single compartment that captures multiple cores and images them together). For example, rather than imaging samples individually to locate calcifications, real-time imaging of multiple cores may be performed to determine either when any calcified tissue has been extracted, or when a threshold amount of calcified tissue has been extracted. The tissue samples may be removed from the RSC and forwarded to a lab for further analysis. Specimen holders for capturing multiple calcifications for simultaneous imaging may include features that facilitate distribution of individual samples within the specimen holder.

Figure 14A:
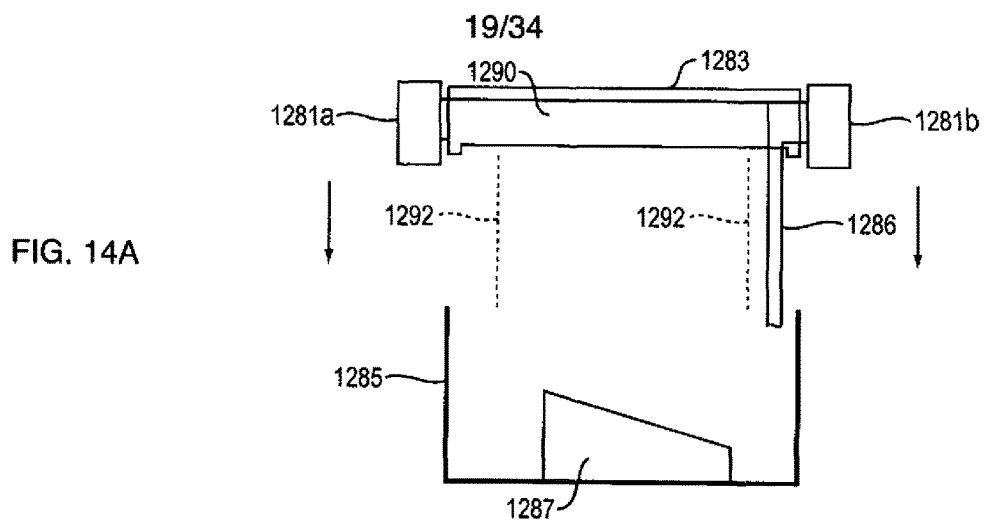
FIG. 14A illustrates a specimen holder which captures multiple samples for simultaneous imaging.

FIG. 14A illustrates a specimen holder which captures multiple samples for simultaneous imaging. The illustrated specimen holder includes a container 1285 and a cap 1283, each of which is made of radiolucent material. An angled or flat ramp 1287 is mounted within the container. The cap 1283 includes an inlet port 1281a and an outlet port 1281b. The inlet port is coupled to the biopsy needle via tubing. The outlet port is coupled to the vacuum console via tubing. The cap 1283 includes a channel 1290 which extends from the inlet port partially into the interior volume of the container. An aspiration tube 1286 extends perpendicularly from the outlet port 1281b of the cap. A cylindrical filter 1292 extends perpendicularly from the cap to the base of the container when the specimen holder is assembled, thereby separating the inlet port from the outlet port.

Figure 14B:
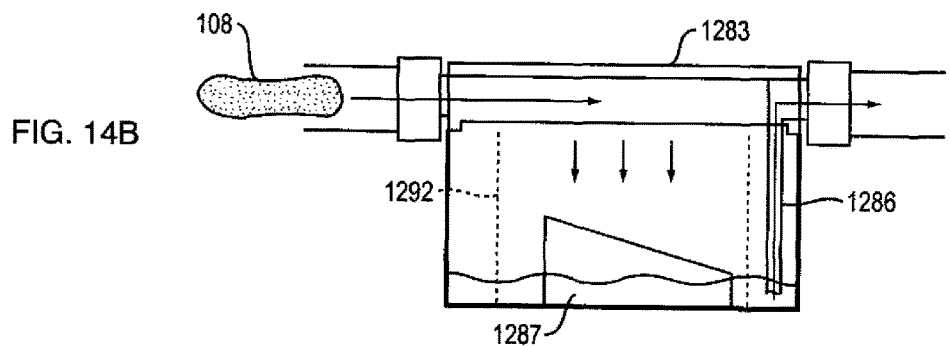
FIGS. 14B through 14C illustrate operation of the sample holder of FIG. 14A.
Figure 14C:
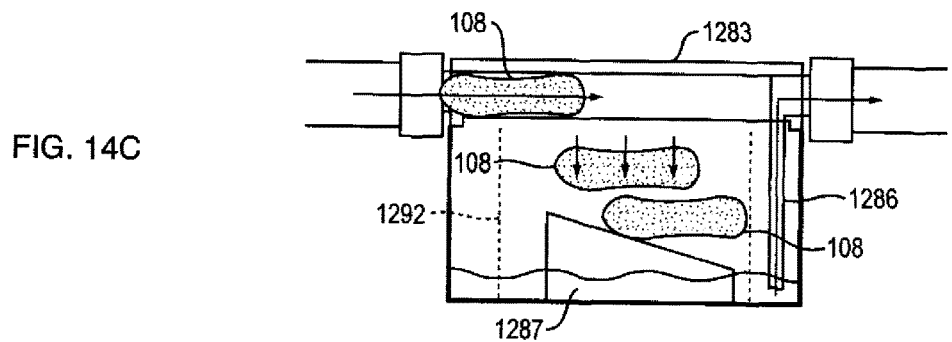

Referring now to FIGS. 14B through 14C, a tissue sample and fluid from the biopsy needle enters the specimen holder through the inlet port, traverses channel 1290, and is deposited on ramp 1287 (or on other tissue samples already deposited on the ramp). Application of vacuum pressure via the aspiration tube removes fluid so as to maintain the fluid level within the container at a level below the ramp and ensures that all saline or fluid remains in the gutter formed around the ramp. Consequently, fluids drain off of tissue samples which have been deposited on the ramp. Separating fluid from the samples is advantageous because the fluid can mask the outline of the core in the image. The tissue sample is prevented from being sucked out of the outlet port by the filter which separates the innermost volume of the specimen holder from the aspiration tube. When a desired number of tissue samples have been collected, the samples are imaged in the specimen holder. This image could be taken after each core, after two cores, or any interval including one at the end of the procedure. This holds true for any of the specimen holders described. The specimen holder and components are designed to reduce interference or any error associated with the analysis (e.g. the design will be radioluscent and of uniform signal in the imaging area if X-ray is used). The cap can then be removed from the container in order to allow removal of the imaged samples.

Figure 16A:
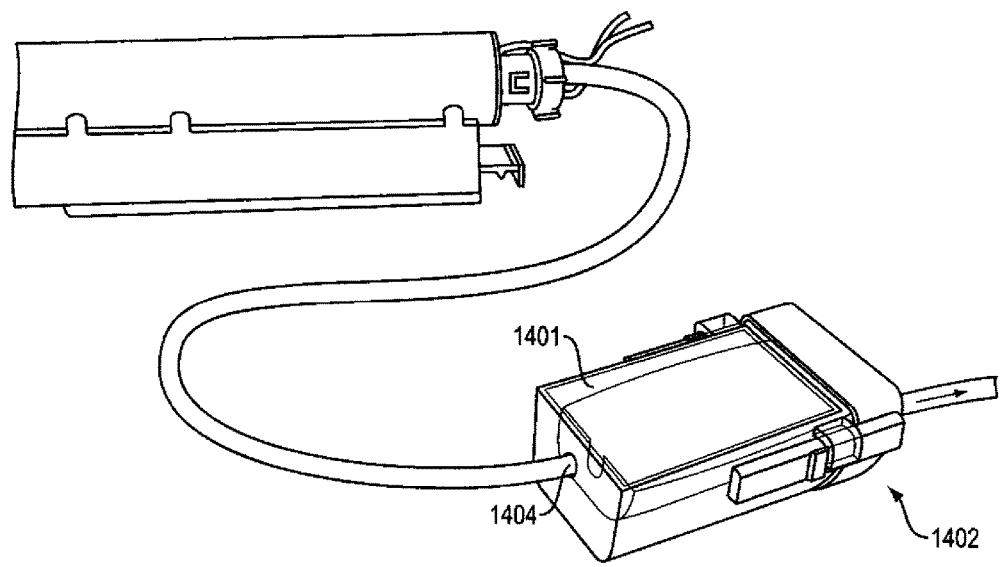
FIGS. 16A, 16B, and 17A through 17C illustrate another alternative embodiment of the specimen holder.
Figure 16B:
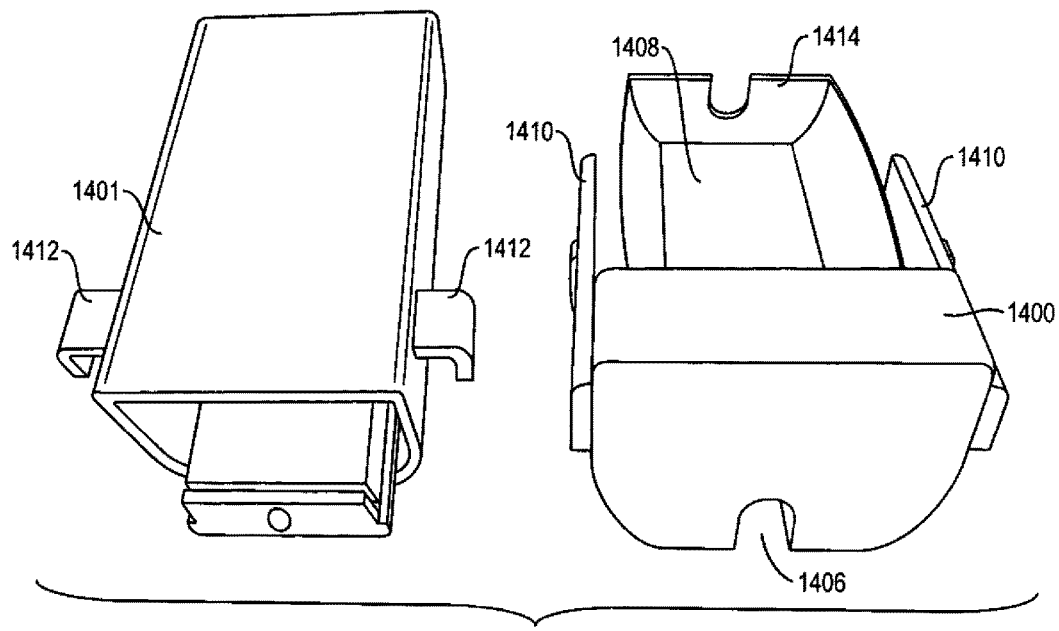
Figure 17A:
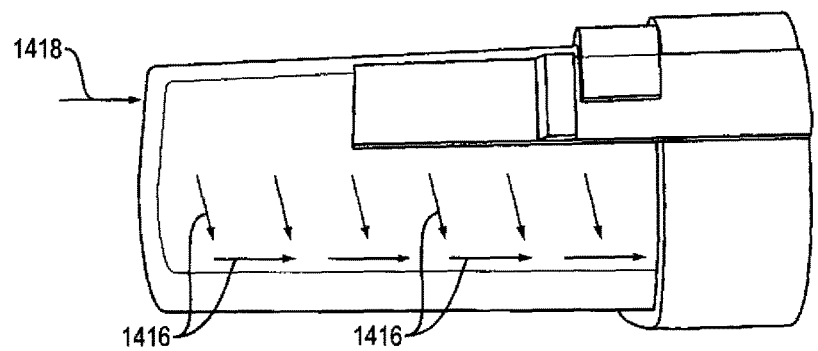
Figure 17B:
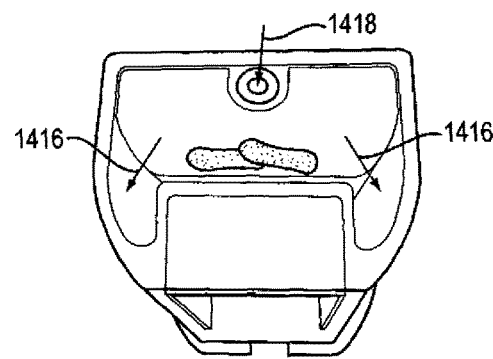
Figure 17C:
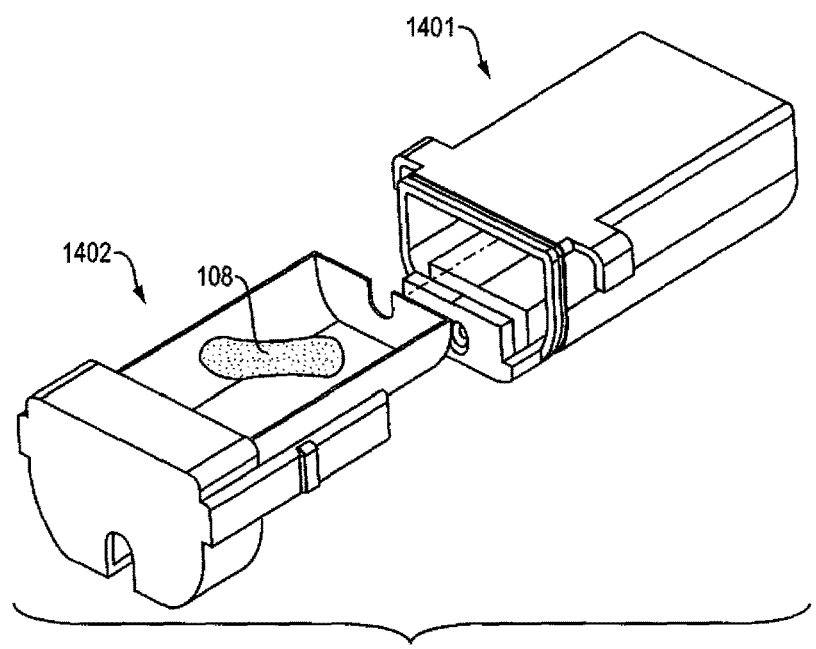

It should be appreciated that all mentioned embodiments of the specimen holder and tissue filter that actively capture and secure tissue are able to be used to capture tissue samples without an inline RSC. For example, tissue samples captured in the carousel type specimen holder described in FIGS. 4a and 4b, or the filter specimen holder described in FIGS. 16-18, along with other embodiments, could be used without an in line analysis type of system. The specimen holder, or a component of, would be removed from the biopsy device and taken to an X-ray system (RSC or Mammography unit) that is typically located outside of the biopsy suite. This still eliminates or reduces the need to manipulate individual cores in preparation for the specimen radiograph. Further, the tissue samples could be imaged both by the in-line RSC and some other device. In addition to helping to avoid manual handling and arrangement, this can help avoid the need for a separate container such as a Petri dish.

Figure 14D:
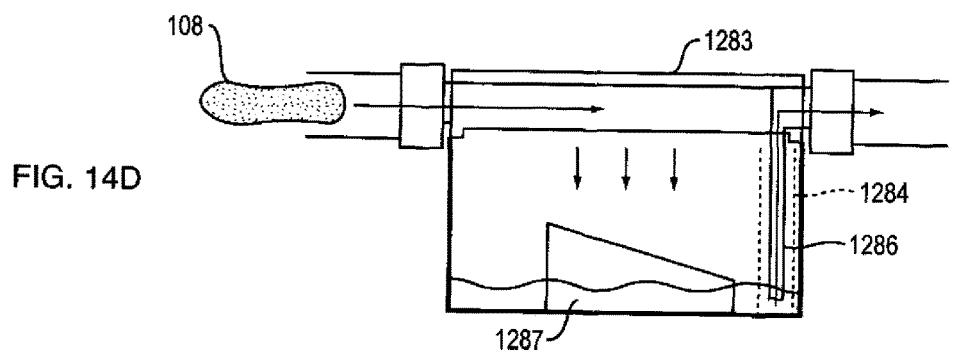
FIG. 14D illustrates an alternate embodiment of the specimen holder in which a cylindrical filter is disposed around the aspiration tube.

FIG. 14D illustrates an alternate embodiment in which a cylindrical filter 1284 is disposed around the aspiration tube 1286. In this alternative embodiment the larger filter 1292 (FIG. 14A) may be omitted. Another variant is a filter across the inlet port of the aspiration tube. Other means for preventing tissue samples from exiting the specimen holder might also be employed.

Figure 15A:
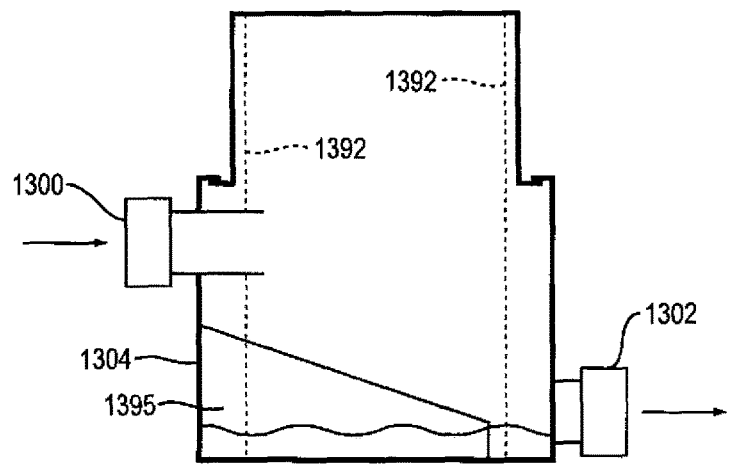
FIGS. 15A and 15B illustrate a variant of the embodiment of FIGS. 14A-14D in which an inlet port and outlet port are integrated with a container.
Figure 15B:
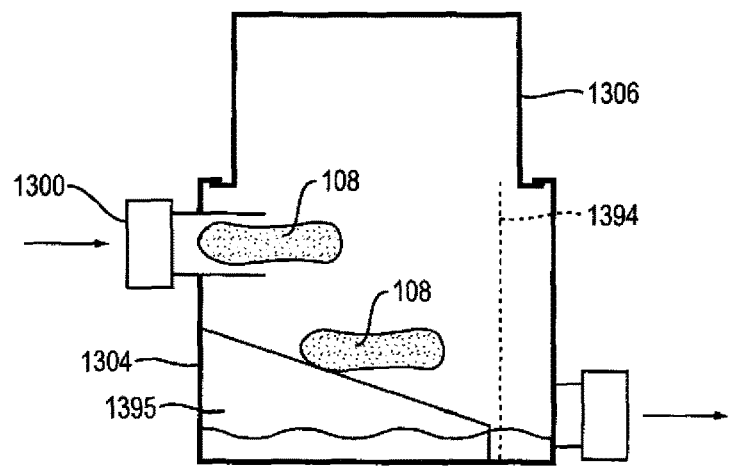
Figure 15C:
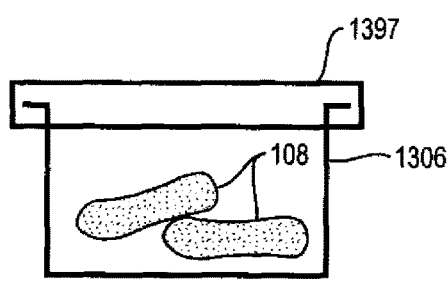
FIG. 15C illustrates a lid for enclosing the samples.

FIGS. 15A and 15B illustrate a variant of the embodiments of FIGS. 14A-14D in which an inlet port 1300 and outlet port 1302 are integrated with a container 1304 (rather than the cap). A cap 1306 can be temporarily affixed to the container during use. The inlet port is offset from the outlet port such that the inlet port is higher than the outlet port when the container is upright. As shown in FIG. 15B, samples 108 entering through the inlet port move through a short interior channel and are deposited onto a ramp 1395, where bio-fluid drains away from the samples into the gutter formed around the ramp. The fluid flows out of the outlet port, which is disposed proximate to the level of the base of the container. Samples are prevented from entering the outlet port by a filter, e.g., a cylindrical filter 1392 or a filter panel 1394. The assembly is radiolucent, and images may be acquired at regular intervals or in response to a trigger condition, for example from timing or a motion detector which detects movement of the cores towards or through the inlet port. When the samples have been imaged and the biopsy completed, either because a desired number of samples has been excised, or because a sufficient number of calcified samples have been detected, the specimen holder may be removed from the RSC. In order to prepare the samples for transport the container is inverted so that the samples fall away from the ramp into the cap due to gravity or applied force. The cap should have sufficient interior volume to accommodate the samples. A lid 1397 is then affixed to the cap in order to enclose the samples as shown in FIG. 15C. Further, formalin could be added such that the cap can serve as a specimen jar.

Another alternative embodiment of the specimen holder is shown in FIGS. 16A, 16B, and 17A through 17C. A tissue tray 1402 with integral end cap 1400 fits into a containing cover 1401. In particular, the specimen holder is assembled by sliding the tissue tray 1402 into the cover 1401 until the end cap is seated against an opening at one end of the cover. Both the tray and cover are manufactured from radiolucent material, such as plastic or the like. The cover 1401 is generally rectangular parallelepiped in shape, comprising a pair of side walls coupled between base and top walls, a distal wall and an opening. The integral end cap 1400 of the tissue tray forms a proximal wall across the opening of the cover when the specimen holder is assembled. An inlet port 1404 is disposed in the distal wall of the cover. An outlet port 1406 is disposed at a proximal portion of the cover. Retaining features such as locking tabs 1410 are disposed on the end cap 1400 for insertion into corresponding locking features 1412 disposed on the outer surface of the cover. The retaining features secure the end cap to the cover such that fluid leakage is inhibited when the specimen holder is assembled. The tissue tray includes a base member 1408, sidewalls extending upward from the base member, and a notched endplate 1414 perpendicularly mounted thereon. The tissue tray functions as a filter such that bio-fluid can drain away from the tray for removal via the outlet port. The width dimensions should also be such that tissue samples cannot pass through the gap between the tissue tray and the cover or flow out of the outlet port.

During a biopsy procedure tissue samples and bio-fluid enter the specimen holder through the inlet port and are deposited in the tissue tray. The base member of the tissue tray may include a drain or filter for allowing fluid to drain away from the captured tissue samples. Consequently, the specimen holder typically contains both air and fluid during a biopsy, both of which flow as shown with arrows 1416, 1418. After the biopsy procedure is complete the tray is removed from the cover by disengaging the retaining features. Analysis of the specimen could be conducted in an in-line type of system as described in FIG. 2, or the tissue tray could be removed and taken to an x-ray system (e.g. Mammography unit or RSC that is not part of the biopsy system).

Figure 18A:
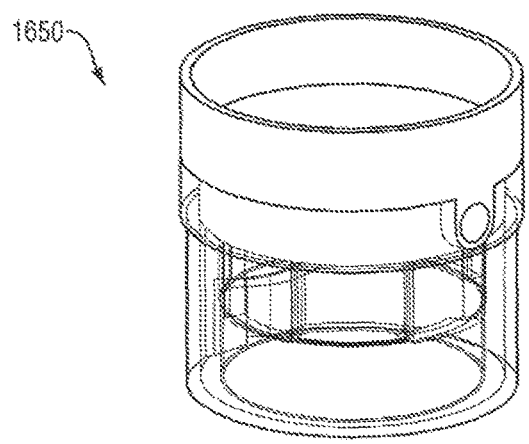
FIGS. 18A, 18B, and 19 illustrate yet another embodiment of the specimen holder.
Figure 18B:
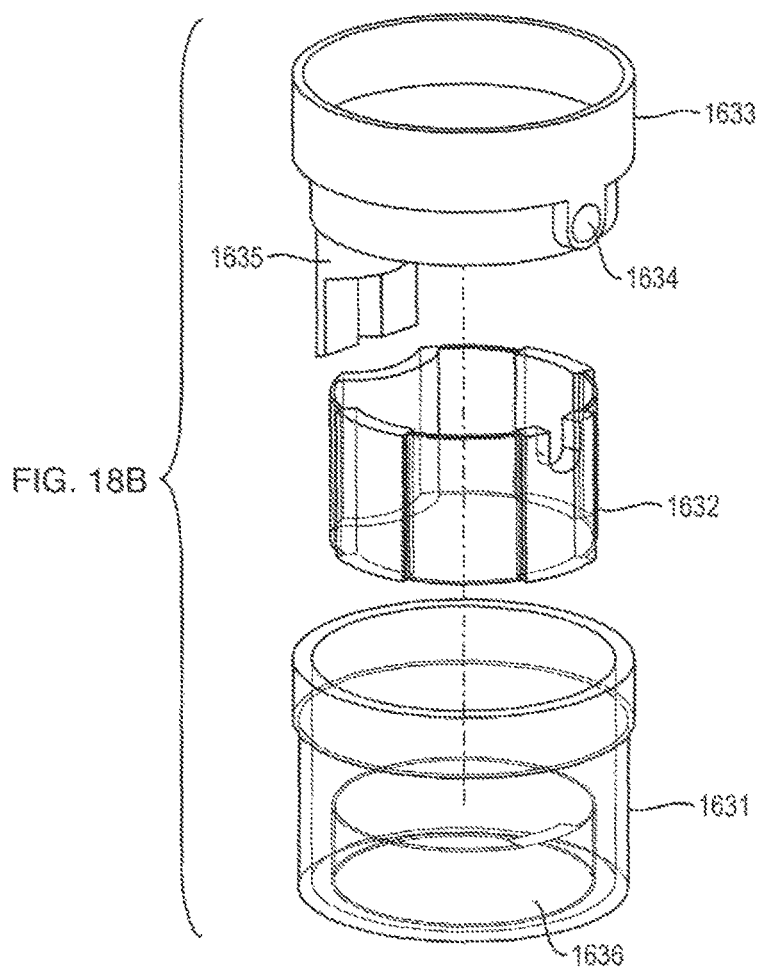

FIGS. 18A and 18B illustrate another embodiment of the specimen holder. The illustrated specimen holder includes a cylindrical container base 1631, a basket 1632 and a cover 1633. A cylindrical stage member 1636 projects from the bottom of the base. The mesh basket 1632 includes roughly cylindrical walls and a mesh base which rests on the stage member. The stage member 1636 has a smaller diameter than the base 1631, thereby forming an annular gutter 1650 into which bio-fluid drained away from captured tissue samples can be collected for removal via an outlet port. A horizontal inlet port 1634 and a vertical outlet port 1635 are incorporated into the cover. The outlet port 1635 includes a tubular conduit and associated structure which, when the specimen holder is assembled, extends into the annular gutter 1650. An indent in the wall of the basket accommodates the outlet port 1635, i.e., enabling the outlet port to extend into the annular gutter 1650. Tissue samples received at the inlet port are deposited into the basket where they are captured. Bio-fluid is drained away from the samples through the mesh base of the basket. The drained fluid collects in the annulus and is removed via the outlet port either through the mesh stage member or directly from the annulus. The outlet port exits the specimen holder through the top of the cover.

Figure 19:
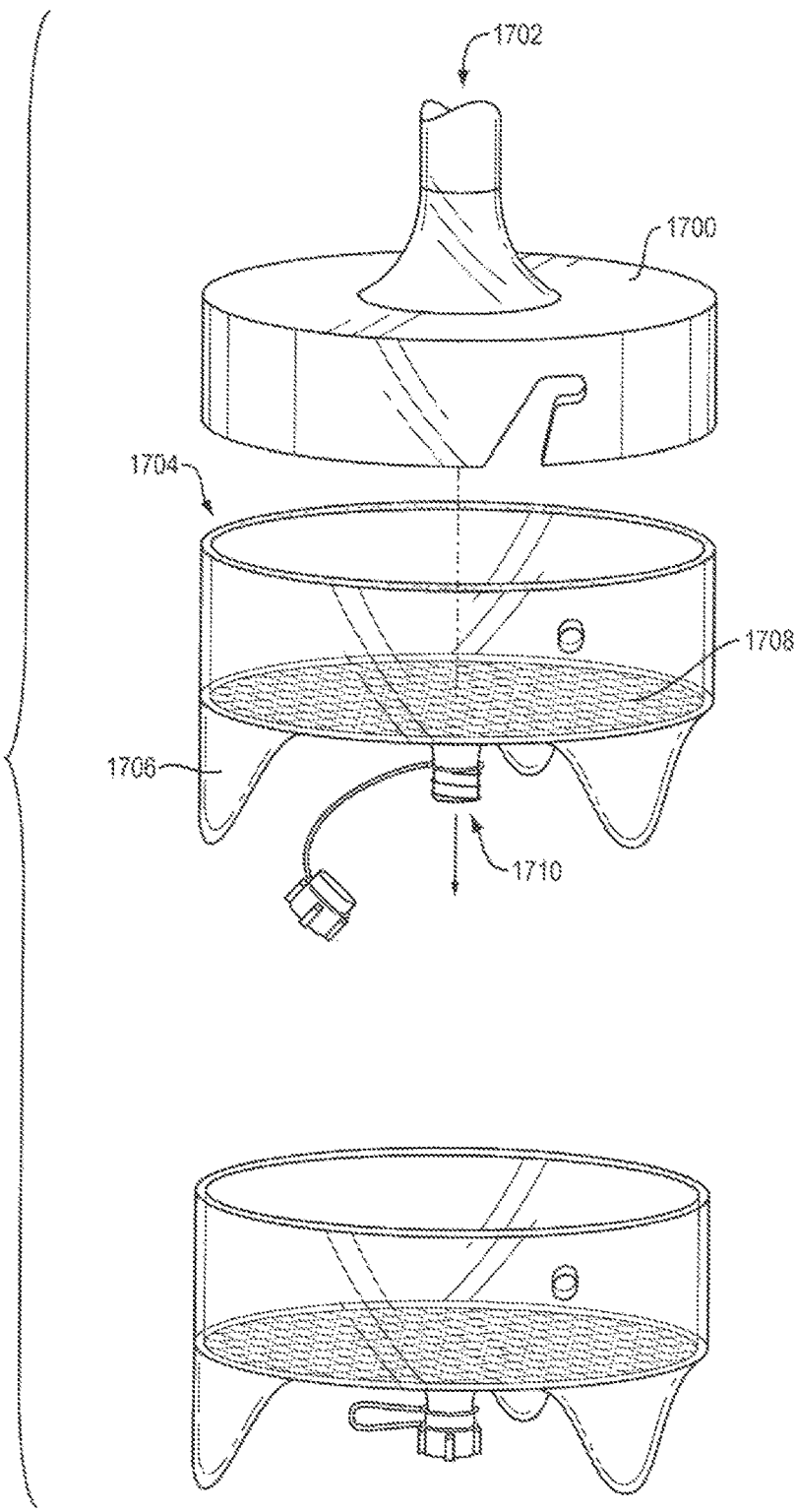

FIG. 19 illustrates an embodiment in which the cover 1700 includes a vertical inlet port 1702 and the basket 1704 includes legs 1706. The basket includes a filter 1708, and is both radiolucent and artifact-free. An outlet port 1710 is below the filter. A gasket may be provided to form a seal between the basket and cover when assembled. Tissue samples introduced via the inlet port are captured in the basket. Bio-fluid is drained away from the captured samples via the output port. Saline flow from the inlet port combined with suction from the outlet port may help to disperse samples across the filter, thereby facilitating delineation of the samples during imaging. An optional cap may be provided to stop fluid drainage through the filter if it is desirable to disconnect the basket from the tubing, e.g., for removal from the RSC.

It should be noted that the specimen holders described above could be used as tissue collection filters 230 (FIG. 2). For example, samples could be temporarily captured for imaging in one embodiment of a specimen holder and captured for transport in the same or another embodiment of a specimen holder.

Figure 20A:
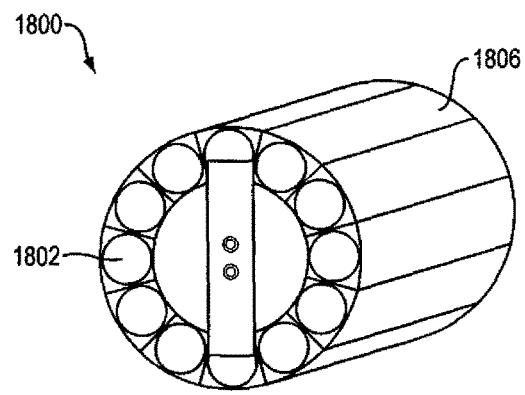
FIGS. 20A through 20C illustrate an alternative embodiment of the specimen holder in which captured samples are automatically arranged for individual identification.
Figure 20B:
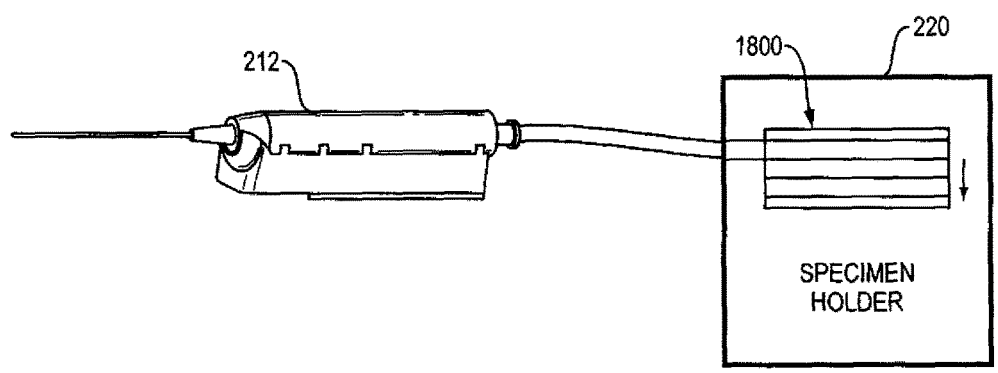
Figure 20C:
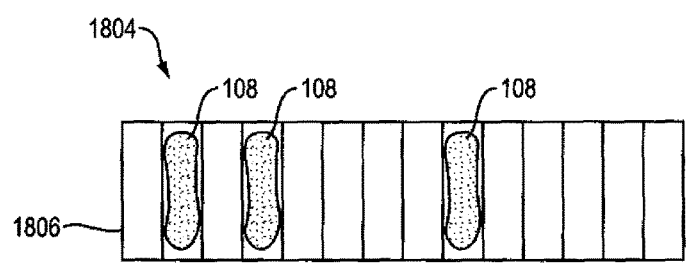

FIGS. 20A through 20C illustrate an alternative embodiment of the specimen holder in which captured samples are automatically arranged for individual identification and matching with images. When samples are randomly distributed within a specimen holder it is sometimes difficult to match each particular sample with a corresponding x-ray image or portion of an image. This can be problematic if, for example, the operator wishes to separate a subset of samples having calcifications. The illustrated specimen holder includes a revolving cylinder 1800 fabricated of radiolucent material with multiple sample containment chambers 1802 arranged in a ring. Each chamber has an inlet and an outlet. The outlet is covered by a mesh filter such that tissue samples do not traverse the chamber but bio-fluid is drained away. An o-ring may be disposed at the inlet of each chamber and at the perimeter of the revolving cylinder to facilitate sealing against an inlet port of the specimen holder, which could be loaded into the RSC. A tissue sample excised with the biopsy device 212 (FIG. 2) travels through tubing into the RSC and is captured in a chamber aligned with the inlet port. The sample is then imaged and the specimen holder is rotated to align an adjacent empty chamber with the inlet port. The procedure is repeated when another sample is captured, although the embodiment is not limited to one sample per chamber. The chambers may be labeled, e.g., with a visual indication of order of capture on the specimen holder, so that images can be matched to samples. Furthermore, the samples need not be imaged individually, e.g., the entire specimen holder could be imaged, including samples captured in some or all of the chambers. Alternatively, the specimen holder could simply be used for sample capture and/or storage. Differential pressure detection mechanisms or other techniques described above can be used to trigger image capture and rotation of the cylinder such that an empty chamber is presented for storage of a subsequently excised sample. Following biopsy, the specimen holder is removed from the RSC. As shown in FIG. 20C the outer ring of the cylinder may be detachable, e.g., with a joint at an interface 1806 between adjacent chambers, so that the ring of chambers may be unwound into a flat configuration 1804 for linear presentation, which is advantageous for a typical radiograph.

Figure 20D:
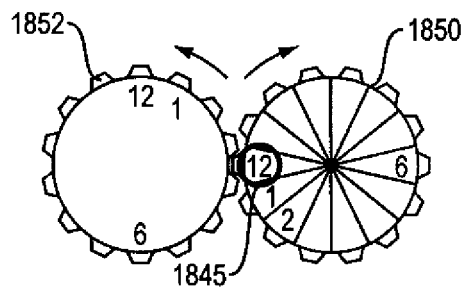
FIGS. 20d, 20e and 20f illustrate a mechanism to synchronize the biopsy device and tissue filter to enable tracking clock position of cores.
Figure 20E:
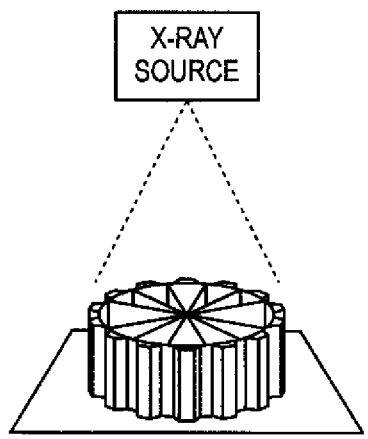
Figure 20F:
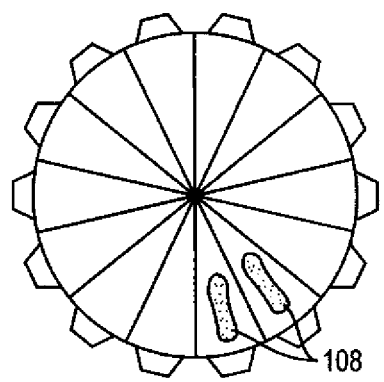

FIGS. 20*d*, 20*e* and 20*f* illustrate a mechanism to synchronize the biopsy device and tissue filter to enable tracking clock position of cores. This enables collecting cores in a manner that tracks the clock position from which each cores was obtained. Currently, if a physician wants to do this, they collect one core at a time and place it into a tray that is separated into clock positions. Various mechanisms could be used to help synchronize a filter 1850 and rotating part of a biopsy device 1852, including but not limited to gears, belts, friction drive, sensors and motors. In the illustrated example gearing maintains the filter in position relative to the biopsy device. For example, a sample taken at 12 o'clock is stored at 12 o'clock because of inlet 1845 position. Rotating the biopsy device 1852 such that the 1 o'clock position rotates the filter such that the 1 o'clock slot is aligned with the inlet port. Consequently, a sample taken at 1 o'clock is stored at 1 o'clock. The positions are marked so that they can be seen with the naked eye, analysis equipment, or both. Further, the filter and device can be oriented in various ways, including but not limited to side-by-side, vertical stacking, and integrating the filter within the device. The filter can be disengaged from the biopsy device and analyzed, or analyzed in the aforementioned in-line approach.

Figure 21A:
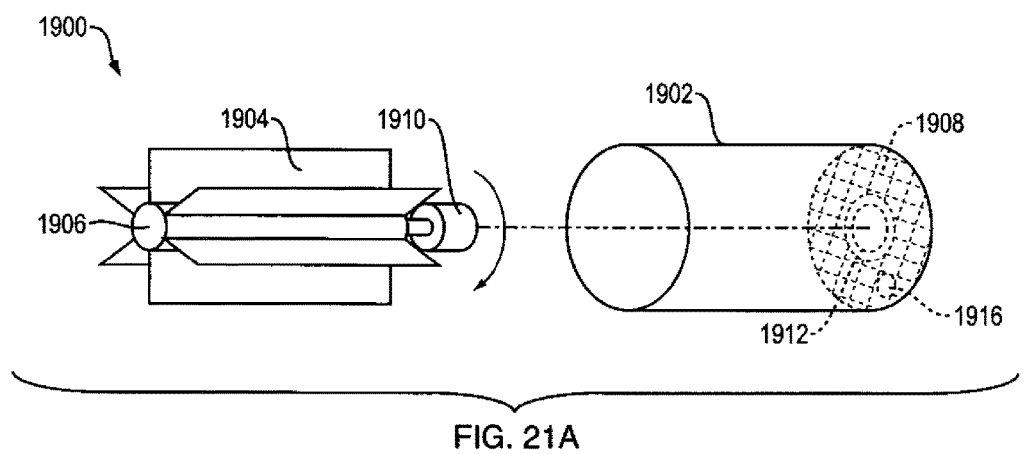
FIGS. 21A and 21B illustrate another variation of a rotating cylinder specimen holder.
Figure 21B:
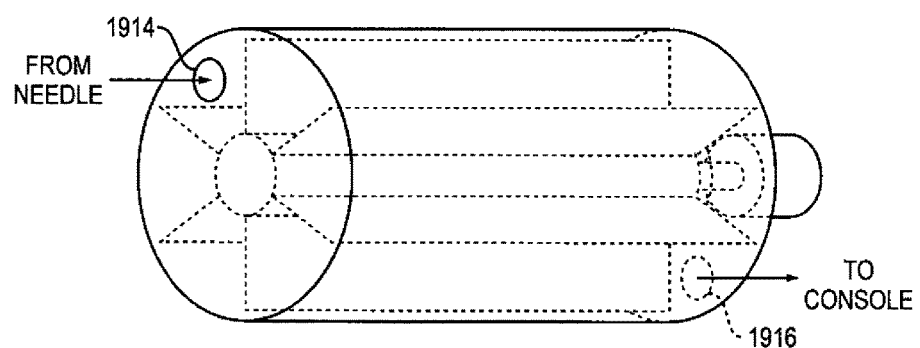
Figure 22A:
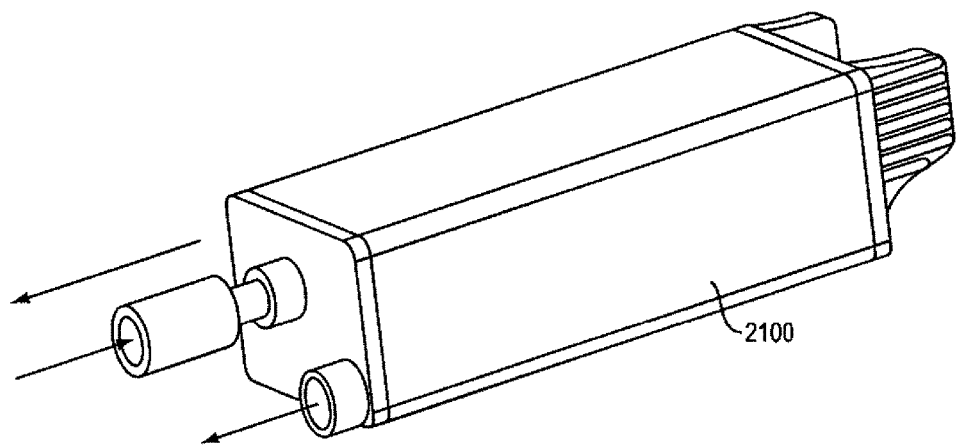
FIGS. 22A through 22D illustrate an alternative compartmentalized specimen holder.
Figure 22B:
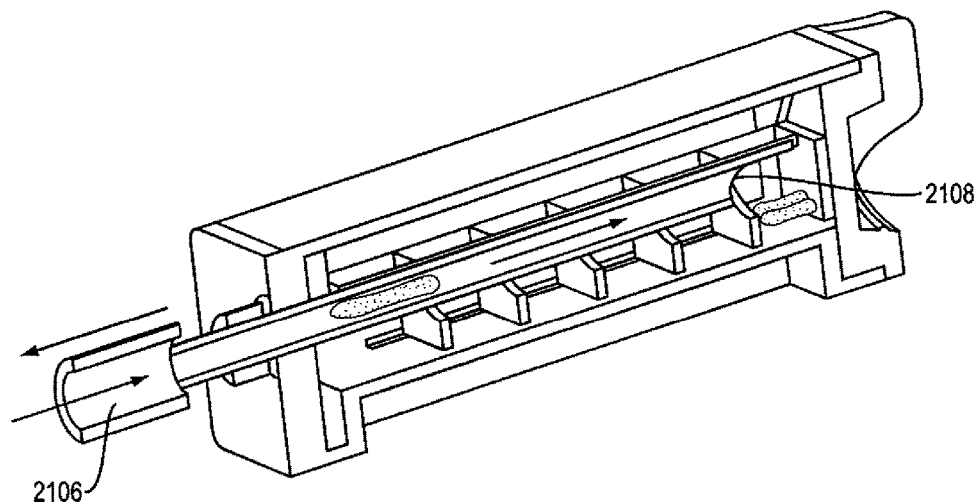
Figure 22C:
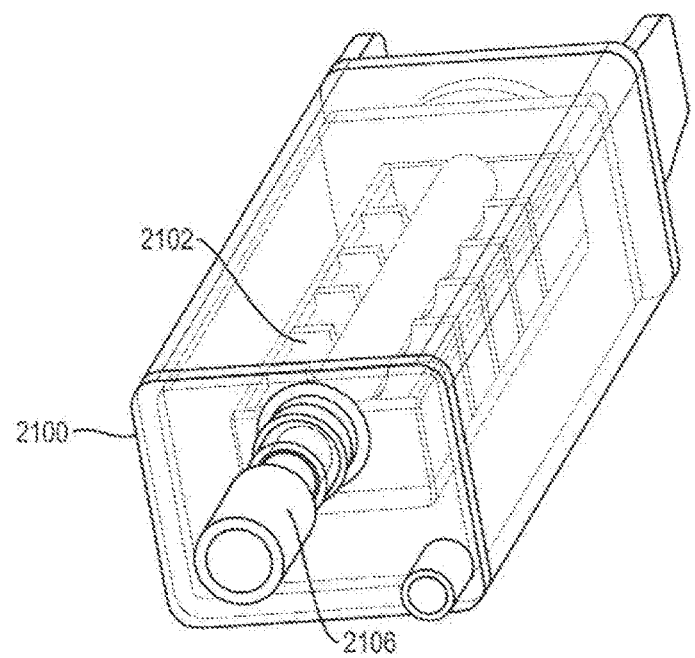
Figure 22D:
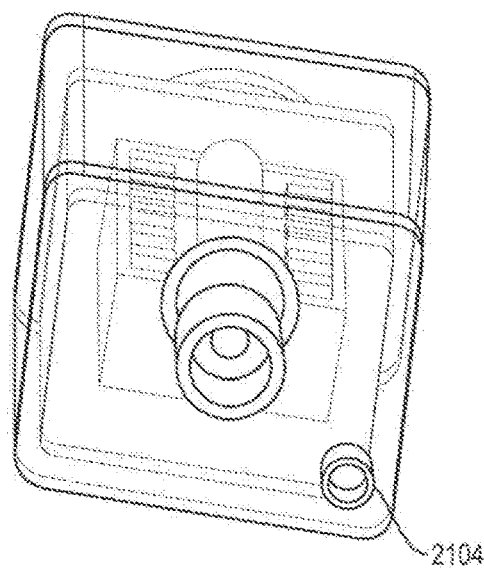

FIGS. 21A and 21B illustrate an alternative revolving cylinder specimen holder. In this embodiment the tissue sample containment chambers are formed by inserting an interior wall assembly 1900 into an outer cylindrical cup 1902. The interior wall assembly includes a plurality of walls 1904 extending from a central axis 1906. A distal edge of each wall relative to the central axis forms a press or close fit against an inner surface of the outer cup, e.g., such that the a tissue sample cannot pass between the interior wall and the cup along the contact surface. At least a portion of the wall assembly 1900 and/or the cylindrical cup 1902 may be porous in nature to permit fluid flow while also preventing traversal by tissue samples. A gear or knob 1910 may be disposed at an end of the central axis of the interior wall assembly to enable rotation of the specimen holder. A distal end of the cup may include a grommeted hole 1912 with seal through which the gear or knob extends upon assembly. The resulting rotating specimen holder functions during biopsy in the manner described above with regard to the embodiment of FIGS. 21A and 21B.

In a variation of the embodiment described above the interior wall assembly 1900 is rotated while the outer cup 1902 is held stationary. In this embodiment the fit between the interior walls and the outer cup should exhibit less friction, although it should also prevent presentation of gaps where a captured sample might be caught during rotation. The bases of the outer cup include, respectively, an inlet port 1914 and an outlet port 1916, both of which are offset from the central axis. The bases may be implemented with removable caps. As a sample enters a chamber it is captured and imaged, following which the interior wall assembly is rotated relative to the outer cup to present an adjacent empty chamber to the inlet port. Imaging may be performed by positioning the specimen holder such that the x-ray source is normal to the proximal base of the specimen holder, and the detector is in a position normal to the distal base of the specimen holder.

FIGS. 22A through 22D illustrate an alternative compartmentalized specimen holder. This embodiment includes a base container 2100 and a filter member 2102 characterized by a row of tissue sample retention compartments. An outlet port 2104 is formed in the base container and an inlet port 2108 is formed in an inlet conduit 2106. The inlet conduit is inserted into the base container through an opening that may include a seal. The seal permits the inlet conduit to be slidably moved further into or out of the interior volume of the base container without fluid leakage. Such linear repositioning is employed to relocate the inlet port in order to selectably deposit a tissue sample in a particular compartment in the row. Operation of the inlet conduit may be coordinated, and the containers marked, such that images can be matched with associated samples.

All of the embodiments described herein that capture tissue, can be used with or without an inline analysis system, such as that described in FIG. 2. If an inline analysis system is not used, the specimen holder, or a portion of, is removed from the biopsy device after sufficient cores are gathered. The cores are then transported for analysis on any other separate system for analysis (RSC, Mammography unit, spectroscopy, MRI, etc). This may require that the specimen holder or portion of is designed to reduce any potential error in the analysis (e.g. radioluscent and homogenous signal if X-ray is used, and saline is removed for X-ray). In addition, the specimen holder of portion of can be capped and serve to keep specimens separated from one another if applicable. If multiple chambers are present in the holder or portion of, they can be labeled to allow correlation to a labeled analysis result for that particular chamber. This aids in communicating to the pathologist or other which cores have an abnormality as determined by the analysis.

Figure 23:
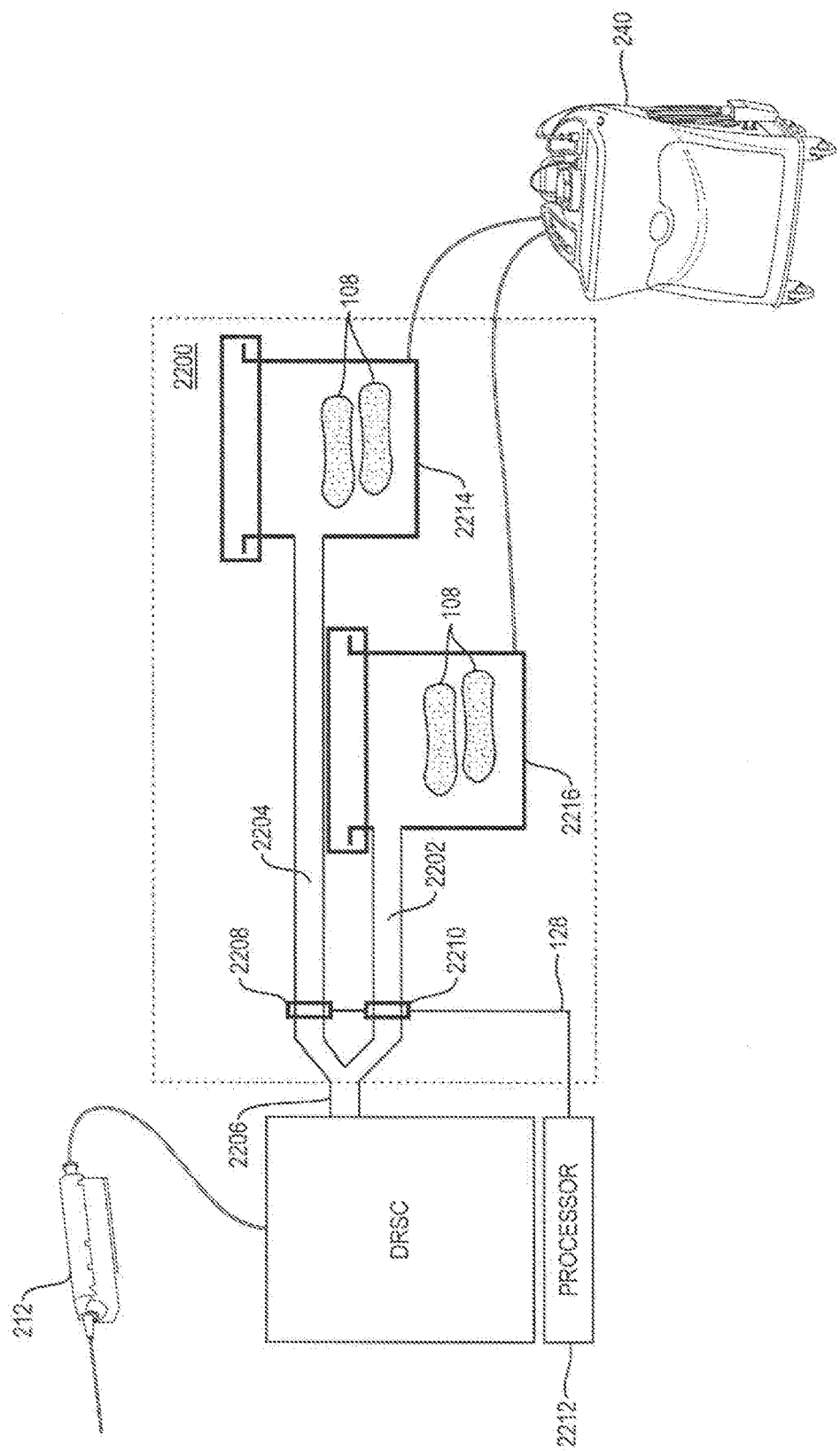
FIG. 23 illustrates a multi-channel tissue sample sorting system.

FIG. 23 illustrates a multi-channel tissue sample sorting system 2200. The system includes a plurality of sample distribution tubes, such as tubes 2202 and 2204, each of which is coupled to a main tube 2206 through which samples travel when exiting the staging area of the RSC. Each distribution tube is coupled to a separate specimen holder or filter/container 2214, 2216. The flow of fluid and samples from the main tube into a particular distribution tube is controlled by valves 2208, 2210, e.g., one valve for each distribution tube, disposed proximate to where the sorting tubes connect to the main tube. Pinch valves or similar devices could be used, although the invention is not limited to any particular type of valve. Tissue samples may be sorted on any desired basis. For example, tissue samples may be sorted based on detection of calcifications. In such an implementation a tissue sample would be imaged in the staging area. The presence of calcifications in the imaged sample could be determined either manually, e.g., by viewing on a monitor and indicating a determination via an interface, or automatically using a processor 2212 and Computer Assisted Detection (CAD) algorithms. The state of one of the valves would then be automatically changed, e.g., opened with a control signal, thereby allowing the sample to move out of the staging area and into a container for samples with calcifications or a container for samples lacking calcifications.

Figure 24:
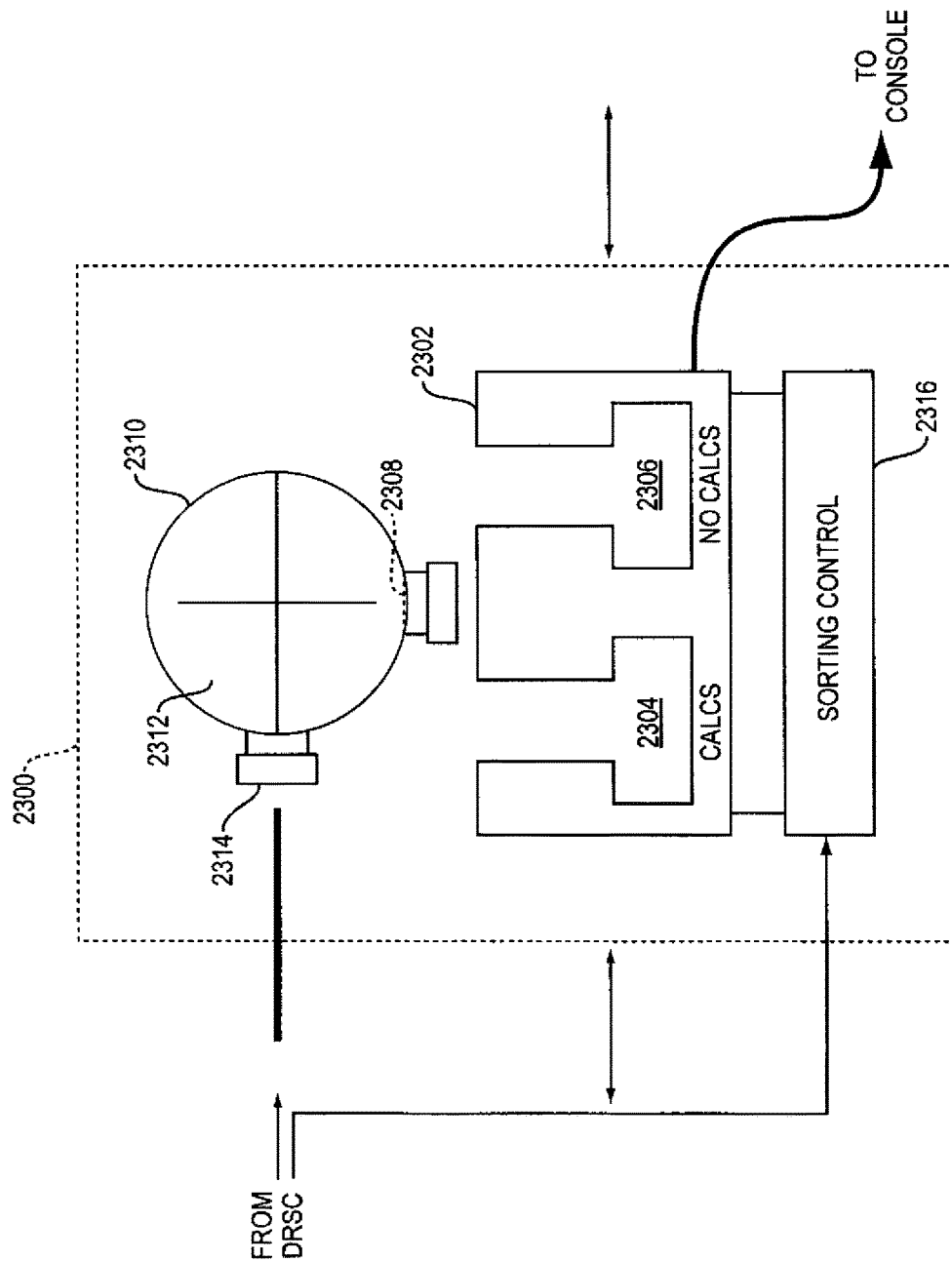
FIG. 24 illustrates an alternative tissue sample sorting system.

FIG. 24 illustrates an alternative tissue sample sorting system 2300. The system could be integrated with the RSC or implemented as a separate system. In this embodiment a tissue sample collector 2302 includes multiple receptacles 2304, 2306 which can be selectively aligned with a port 2308 in order to deposit a tissue sample into an appropriate receptacle. A multi-compartment rotating wheel assembly 2310 can be used to facilitate depositing of the tissue sample in the appropriate receptacle. For example, an imaged sample can be flushed from the specimen holder in the RSC even before image analysis has been performed. The flushed sample flows from the RSC into a compartment 2312 of the wheel assembly aligned with an inlet port 2314. The wheel assembly is then rotated to prepare to receive a subsequent sample. Once the sample has been processed to determine whether it includes calcifications or some other characteristic, a sorting controller 2316 receives tissue classification information from the RSC and uses this information to selectively shift the tissue sample collector 2302 into position such that the outlet port 2308 of the wheel assembly is aligned with the appropriate receptacle, 2304 or 2306. The wheel is then rotated until the compartment containing the sample is aligned with the outlet port 2308, and the sample is deposited in the appropriate receptacle. This advantageously allows sample excision and imaging to continue even if image processing is relatively slower because the tissue samples are buffered in the wheel assembly between the specimen holder and receptacles pending classification results. The wheel may be implemented with a number of compartments calculated to enable a full set of biopsy samples to be excised and imaged before sorting occurs.

FIG. 25 illustrates a variation 2352 of the embodiment of FIG. 24. In this variation a sample collector 2350 with multiple compartments 2354, 2356 is moved rotationally rather than linearly in order to selectively align a compartment with the outlet port 2358 of the wheel assembly. The illustrated cylindrical sample collector includes a first compartment 2354 for storing tissue with calcifications and a second compartment 2356 for storing tissue samples without calcifications. The sorting control 2360 rotates the cylinder in response to the tissue classification information from the RSC. The system could be integrated with the RSC or implemented as a separate system.

Figure 26A:
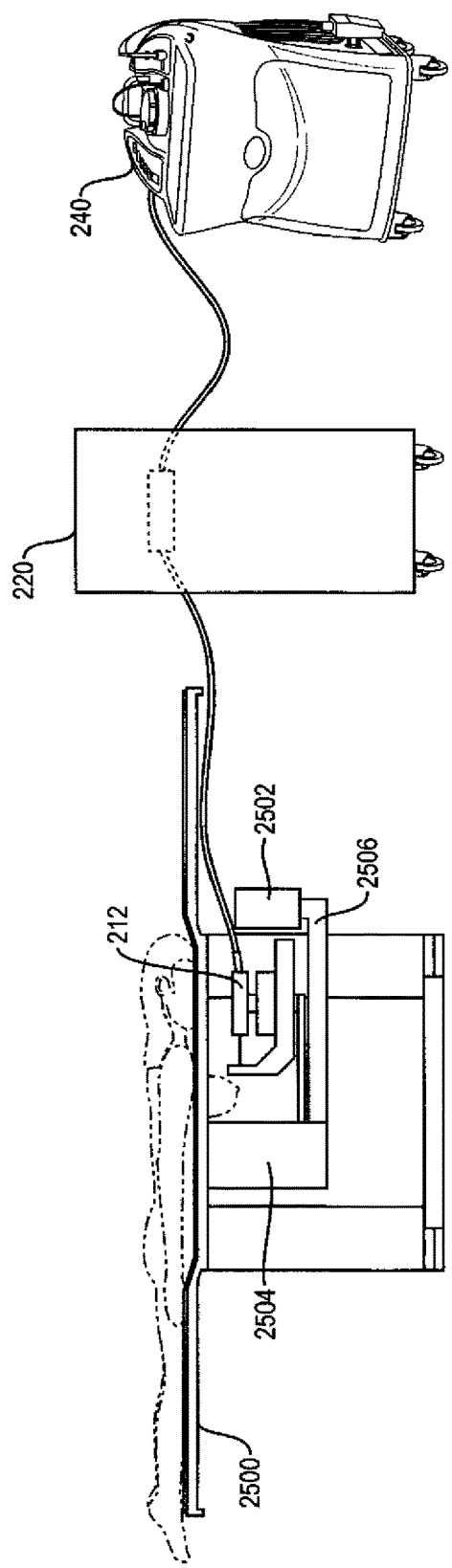
FIG. 26A illustrates use of the biopsy suite.

FIG. 26A illustrates use of a biopsy suite including aspects of the invention. The biopsy device 212 is mounted below a biopsy table 2500, such as the MultiCare™ Platinum prone breast biopsy table provided by Hologic, Inc., Bedford Mass. The table includes an x-ray source 2502 oriented normal to a detector 2504, and rotatably mounted on a rotating c-arm 2506 for pivoting +/−15 degrees for capturing stereotactic images. Tubing couples the biopsy device 212 to the RSC 220, which is shown to include an integrated specimen holder for capturing tissue samples for the purposes of imaging, and calcification detection, and separation/sorting of tissue.

Figure 26B:
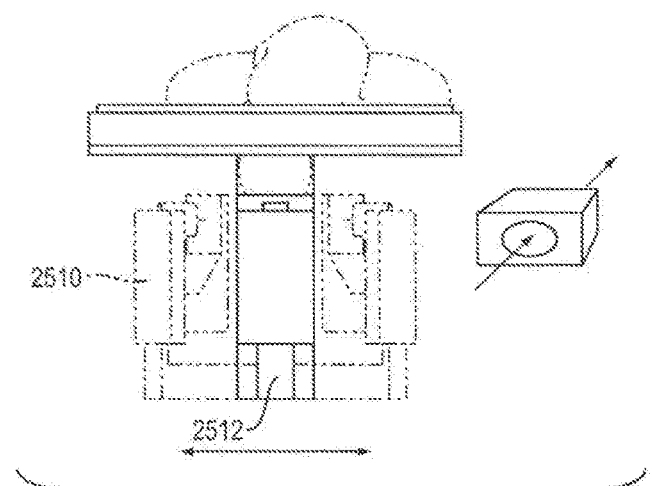
FIGS. 26B and 26C illustrate an alternate embodiment of the biopsy suite of FIG. 26A.
Figure 26C:
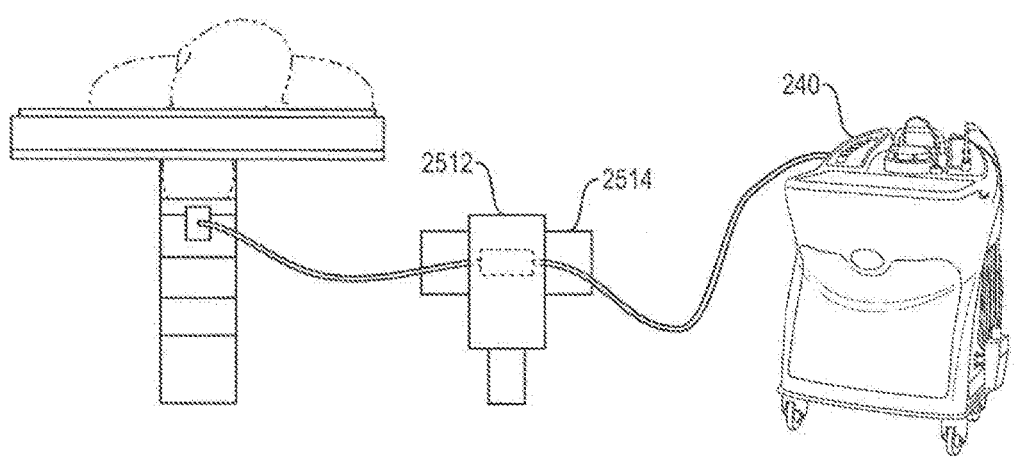

FIGS. 26B and 26C illustrate an alternate embodiment of the biopsy suite. In this embodiment an x-ray source 2510 serves the dual purpose of an x-ray source for stereotactic imaging, and as the x-ray source for calcification visualization. The x-ray source 2510 is mounted on C-arm 2512, pivoting between a +/−15 degree orientation for stereotactic localization of the lesion. Following localization, the source is further pivoted away from the table and coupled to an x-ray shield 2514. Mounted within the x-ray shield is the tissue sample holder. During biopsy, tissue samples travel from the needle to the tissue sample holder, where images are captured. The x-ray shield enables passage of the x-rays through the tissue samples while shielding the operator from exposure. Such an arrangement may reduce the overall cost of a biopsy and visualization system by reducing the number of x-ray sources.

Accordingly various components that may be included in a real-time specimen radiography system have been shown and described, including a RSC with mechanisms for determining when a tissue sample is approaching or has arrived at a staging area, mechanisms for automatically triggering image acquisition, specimen holders capable of staging singular or multiple cores for imaging, tissue sorting mechanisms with the capability of sorting tissue samples using tissue classification information received from the RSC and a display and user interface which allows the operator to dynamically control image acquisition parameters, use CAD tools on acquired images, manipulate and mark images in real time and monitor status. The present invention removes or reduces the need for manual manipulation of specimens from biopsy to placement in formalin, thereby increasing the speed with which procedures can be performed, potentially reducing the amount of tissue that needs to be excised (as the medical professional will know when it has excised appropriate tissue) and increasing the likelihood of getting the target calcifications.

Additionally biopsy device adapted for use with a real-time specimen radiography system has been shown and described and may include a plurality of ports including vacuum port, saline line, and optional additional vent port for venting a cannula of the biopsy device to assist transport of excised tissue into the staging area of the imaging device.

Although embodiments of the inventions have been described in connection with radiographs, other analysis may include imaging and non-imaging based analysis including but not limited to PET, PEM, MRI, ultrasound, x-ray diffraction or any other analysis method.

Although certain embodiments are described for capturing and imaging multiple cores together, variations are contemplated. For example, rather than taking one image of a group of cores it may be desirable to obtain an image after each core is captured, or alternatively after each n cores are captured. For example, an image might be taken of a $1^{st}$ core after it is captured, then when a second core is captured a second image taken of the $1^{st}$ and $2^{nd}$ cores, and so forth. It is also contemplated that the system could be reconfigurable to implement any variant preferred by the operator. This applies for specimen holders that separate each core via multiple chambers and for specimen holders that catch all specimens in one single chamber.

It should also be noted that the specimen holder and/or filter could have some radiopaque markings on the periphery to aid the user in correlating the image to the specimen chamber, e.g., to pick out the cores with calcifications. For example, cores could be separated into a multi chamber filter with markings A thru K (or other markings) that are radiopaque and visible to the naked eye as part of the specimen holder (e.g., Carousel or Linear). Saline is automatically drained from cores and at least one radiograph taken. A through K will be visible on radiographs corresponding to the chambers. It is then easy for the operator to determine which chambers have cores containing calcifications, remove the filter, place a lid on filter, place into formalin, and mark which chambers have calcifications on the label. This advantageously helps communicate to the pathologist which cores have calcifications and has utility independent of real time specimen radiography. Alternatively, the tissue filter could be labeled and visible to the naked eye (e.g. filter labeled 1 through 12), and another feature of the filter (e.g. distinct notch, or other) could be used by the analysis unit to track and label each analysis output to correlate with the filter label (e.g. analysis output labeled 1 through 12)

With regard to the indexing features, it should be noted that individual slots or chambers could be indexed manually or automatically. For example, a motor and controller, or other energy source (pneumatic, etc) could be used to move parts associated with the specimen holder and/or input in order to achieve indexing. Timing for indexing could be based on operator observation and manual actuation (e.g. user rotates by hand), indirect manual actuation (e.g., pushing a button that prompts an action), or automated actuation, (e.g., geared to device rotation, timing from console, pressure monitor, motion of cores).

The specimen holders and features associated therewith may have utility apart from imaging systems. For example, indexing, separation, marking, draining fluid and other functions provided by the various specimen holder features described above are advantageous apart from imaging. Further, specimen holders which can be capped, function as a specimen jar or otherwise include a part or parts that help avoid handling individual samples such as covers which keep specimens in particular chambers are advantageous apart from imaging. The cores should be easily removed and placed into formalin after the procedure, e.g., a one handed, possibly two-handed, procedure. It should be noted that many designs are 2 piece to facilitate a one handed procedure. One hand to grasp the specimen holder, and the other hand to remove the tissue filter. Further, the filter may be capable of being removed and placed on a typical mammography system, or in a specimen radiograph system, and be imaged, e.g., carousel design allows removal of filter that can be placed on Mammography Unit for x-ray. It should be noted that some designs intentionally keep the fluid lines in one part of the specimen holder, such that the other part of the specimen holder can be removed, house the cores, and facilitate transport.

The specimen holders may be characterized by features which facilitate analysis and remove or reduce any potential error induced by the holder. For example, radioluscent materials may be used. Further, homogeneous wall thickness or volume×density of each pixel across the specimen holder may be homogeneous. This helps ensure that the specimen holder shows up as a homogenous area of contrast on the X-ray image if imaged alone. It should also be noted that certain embodiments avoid walls, ports, etc being in the X-ray field of view.

As discussed above, venting cores increases the speed at which they travel out of the biopsy system. Without venting, a vacuum lock is created on the cavity side of the core, and the core may stop moving. This vacuum lock can be relieved with saline venting. The saline vent allows the core to move through the device at a relatively slower pace which can be expedited by venting with air instead of saline. The saline/vacuum system (from the saline source to the cavity side of the core as it moves back to the filter) can be opened to the atmosphere to move the core quickly, i.e. air vent. If this is done, the core moves quickly and is vented by atmosphere instead of saline. Thus, less saline or no saline may be pulled from the bag while this vent to atmosphere is open. However, the air vent may need to be closed prior to the next biopsy cycle to rebuild vacuum levels. Alternatively, the air could replace the saline source. Thus, all venting would be done by atmosphere as opposed to saline or fluids.

Although stopping movement of tissue samples for imaging is described, it is contemplated that a tissue sample could be slowed for analysis or imaged without being slowed. For example, an image or scan could be captured as tissue passes through a field of view.

Although tubing is described for transporting tissue between the biopsy device and the RSC it is contemplated that other means could be utilized, e.g., mechanical systems such as a conveyor belt, transported by withdrawing or moving the hollow cutting cannula or the piercing cannula with core disposed within, using pressure to drive the core out, etc, or combination of. Similarly, the invention is not limited to use with a vacuum.

Those skilled in the art will understand that features described herein may be used in different combinations to produce other embodiments. For example, any form of analysis might be used, including but not limited to x-ray, MRI, PET, Ultrasound, spectroscopy, X-ray diffraction, OCT, etc. Also, any means of getting tissue form device to specimen holder may be used, including but not limited to vacuum, conveyor belt, moving cannula with tissue disposed within, etc or combination thereof. Tissue can be artifact free for any imaging in area of analysis. For example, for x-ray, radiolucent and artifact free in analysis area. Embodiments could be used in line as described with RSC or with external analysis unit, e.g., mammography unit. The entire specimen holder could be removed and used e.g., capping the inlet and outlet. It could also be filled with formalin. Also, a portion of the specimen holder (tissue filter) could be removed. The specimen holder could be capped to keep cores in their individual chambers. Also, the specimen holder or filter may be designed to be placed in formalin jar. The entire specimen holder could be analyzed, or a small portion could be analyzed and then the holder could be indexed to analyze the next region or chamber. Analysis could be performed after each cycle, or after n cycles. The sequence of events could be based on the presence of the core, or based on set cycle time. Presence of the core could be detected by motion, pressure differential, etc. Cycle time could be based on the biopsy device and console. Events could include indexing the chamber, imaging the core, controlling venting, releasing cores, etc. The process could be automated, manual or hybrid manner. Similarly, the chamber can be indexed in any manner, and imaging can be done and cores could be moved in any manner. Further, any embodiment can include features to remove liquid from the samples. Any filter could be uniquely marked/identified to correlate with the analysis images such that each analysis can be correlated to an individual chamber. Markings could be radiopaque or non radiopaque. Markings could be geometry based (nubs, etc). Venting with saline or air is optional; either facilitate removal of the tissue. Air can expedite the travel. Cores do not need to be stopped to be analyzed; they could be scanned as they pass through. Designs can include features to allow analysis substantially free of artifacts, e.g., radioluscent materials, fluid drainage, homogenous wall thickness or volume× density of each pixel across the specimen holder may be homogeneous, avoidance of walls, ports, etc being in the X-ray field of view.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. A method for tissue biopsy and imaging, comprising:
   extracting a tissue sample using a biopsy device;
   aspirating the tissue sample from the biopsy device through a flexible tissue aspiration line into a tissue holding compartment of a tissue sample holder positioned in a fluid communication path between the biopsy device and a vacuum source, wherein the tissue holding compartment is aligned with an outlet of the tissue aspiration line to receive the tissue sample;
   while the tissue sample holder remains positioned in the fluid communication path between the biopsy device and vacuum source, moving the tissue sample holder to position the tissue holding compartment, including the tissue sample, within an imaging field of an imaging system; and
   acquiring an image of the tissue sample using the imaging system.

2. The tissue biopsy and imaging method of claim 1, further comprising displaying the tissue sample image.

3. The tissue biopsy and imaging method of claim 1, further comprising using an image processor to analyze the tissue sample image.

4. The tissue biopsy and imaging method of claim 1, wherein the tissue sample holder is incorporated within or otherwise operatively coupled with the imaging system.

5. The tissue biopsy and imaging method of claim 1, wherein the tissue sample holder is moved using an automated system that rotates the tissue sample holder relative to the outlet of the tissue aspiration line in order to position the tissue holding compartment and tissue sample within the imaging field.

6. The tissue biopsy and imaging method of claim 1, wherein the tissue sample comprises a first tissue sample, the method further comprising
   prior to moving the tissue sample holder to position the tissue holding compartment, including the first tissue sample, within the imaging field of the imaging system, extracting a second tissue sample using the biopsy device; and
   aspirating the second tissue sample from the biopsy device through the tissue aspiration line and into the tissue holding compartment,
   wherein acquiring an image of the first tissue sample comprises acquiring an image of both the first and second tissue samples together in the tissue holding compartment.

7. The tissue biopsy and imaging method of claim 1, the tissue sample holder comprising a plurality of tissue holding compartments, wherein the tissue sample holder is movable relative to the outlet of the tissue aspiration line so as to selectively align a respective tissue holding compartment with the outlet of the tissue aspiration line.

8. The tissue biopsy and imaging method of claim 7, wherein the tissue sample comprises a first tissue sample that is aspirated into a first tissue holding compartment of the tissue sample holder, and wherein moving the tissue sample holder to position the first tissue holding compartment within the imaging field simultaneously aligns a second tissue holding compartment of the tissue sample holder with the outlet of the tissue aspiration line.

9. The tissue biopsy and imaging method of claim 8, wherein the first and second tissue holding compartments are adjacent one another.

10. The tissue biopsy and imaging method of claim 8, further comprising
    extracting a second tissue sample using the biopsy device;
    aspirating the second tissue sample from the biopsy device through the tissue aspiration line and into the second tissue holding compartment;
    moving the tissue sample holder in order to position the second tissue holding compartment, including the second tissue sample, within the imaging field of the imaging system;
    acquiring an image of the second tissue sample using the imaging system, and
    displaying the image of the second tissue sample.

11. The tissue biopsy and imaging method of claim 10, wherein the image of the first tissue sample is displayed prior to extracting the second tissue sample.

12. The tissue biopsy and imaging method of claim 10, wherein the images of the first and second tissue samples are displayed simultaneously on a single display.

13. A method for tissue biopsy and imaging, comprising:
    extracting a first tissue sample using a biopsy device;
    aspirating the first tissue sample from the biopsy device through a flexible tissue aspiration line into a first tissue holding compartment of a tissue sample holder positioned in a fluid communication path between the biopsy device and a vacuum source, wherein the first tissue holding compartment is aligned with an outlet of the tissue aspiration line to receive the tissue sample;
    while the tissue sample holder remains in the fluid communication path between the biopsy device and the vacuum source, moving the tissue sample holder relative to the flexible tissue aspiration line to align a second tissue holding compartment of the tissue sample holder with the outlet of the tissue aspiration line;
    extracting a second tissue sample using the biopsy device and aspirating the second tissue sample from the biopsy device through the flexible tissue aspiration line into the second tissue holding compartment;
    while the tissue sample holder remains in the fluid communication path between the biopsy device and the vacuum source, acquiring an image or respective images of the first and second tissue samples using an imaging system operatively coupled with the tissue sample holder; and
    displaying the image or respective images of the first and second tissue samples.

14. The method of claim 13, wherein moving the tissue sample holder to align the second tissue holding compartment with the outlet of the tissue aspiration line, simultaneously positions the first tissue holding compartment in an imaging field of the imaging system.

15. The tissue biopsy and imaging method of claim 13, further comprising:
correlating the first tissue holding compartment with a first rotational angle of a cutting window of the biopsy device; and
correlating the second tissue holding compartment with a second rotational angle of the cutting window of the biopsy device.

16. A method for tissue biopsy and imaging, comprising:
extracting a plurality of tissue samples in succession using a biopsy device;
aspirating the extracted tissue samples from the biopsy device through a flexible tissue aspiration line into respective tissue holding compartments of a tissue sample holder positioned in a fluid communication path between the biopsy device and a vacuum source;
while the tissue sample holder remains positioned in the fluid communication path between the biopsy device and the vacuum source, acquiring one or more images of the tissue samples using the imaging system, wherein the one or more images include indicia identifying respective tissue holding compartments.

17. The tissue biopsy and imaging of claim 16, wherein the indicia comprises a visual indication of an order of acquisition of tissue samples contained in the respective tissue holding compartments.

18. The tissue biopsy and imaging of claim 16, wherein the indicia comprises a visual indication correlating the tissue holding compartments with a respective rotational angle of a cutting window of the biopsy device at a time when a respective tissue sample contained in the tissue holding compartment was extracted.

19. The tissue biopsy and imaging method of claim 16, further comprising adjusting a rotational orientation of the tissue sample holder as the extracted tissue samples are received into respective tissue sample holding compartments therein, so that the extracted tissue samples are held in the tissue sample holder in a same relative rotational position as they were extracted.

20. The tissue biopsy and imaging method of claim 16, further comprising using an image processor to analyze the one or more tissue sample images, wherein the indicia comprises information derived from the tissue sample image analysis.

* * * * *